US006235280B1

(12) United States Patent
Chatterjee et al.

(10) Patent No.: US 6,235,280 B1
(45) Date of Patent: *May 22, 2001

(54) METHODS OF DELAYING DEVELOPMENT OF CEA-ASSOCIATED TUMORS USING ANTI-IDIOTYPE ANTIBODY 3H1

(76) Inventors: Malaya Chatterjee, 2400 The Woods La., Lexington, KY (US) 40502; Kenneth A. Foon, 800 Rose St., Lexington, KY (US) 40536; Sunil K. Chatterjee, 2400 The Woods La., Lexington, KY (US) 40502

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/838,692

(22) Filed: Apr. 9, 1997

Related U.S. Application Data
(60) Provisional application No. 60/044,455, filed on Apr. 12, 1996.

(51) Int. Cl.[7] .................... A61K 39/395; C07K 16/00
(52) U.S. Cl. ...................... 424/131.1; 530/387.2
(58) Field of Search ................ 424/131.1; 530/387.2

(56) References Cited

U.S. PATENT DOCUMENTS

| | | |
|---|---|---|
| 4,436,728 | 3/1984 | Ribi et al. |
| 4,726,947 | 2/1988 | Shimada et al. |
| 5,057,540 | 10/1991 | Kensil et al. |
| 5,077,284 | 12/1991 | Loria et al. |
| 5,171,568 | 12/1992 | Burke et al. |
| 5,407,684 | 4/1995 | Loria et al. |
| 5,550,026 | 8/1996 | Yamaguchi. |

FOREIGN PATENT DOCUMENTS

| | | |
|---|---|---|
| WO 91/01990 | 2/1991 | (WO). |
| WO 91/11465 | 8/1991 | (WO). |
| WO 91/16924 | 11/1991 | (WO). |
| WO 92/16231 | 10/1992 | (WO). |
| WO 96/20219 | 7/1996 | (WO). |

OTHER PUBLICATIONS

Bhattacharya et al., "Idiotypic antibody immunotherapy of cancer" *Cancer Immunol. Immunother.* (1994) 38:75–82.
Bhattacharya–Chatterjee et al., "Murine monoclonal anti–idiotype antibody as a potential network antigen for human carcinoembryonic antigen" *J.Immunol.* (1990) 145:2758–2765.
Bhattacharya–Chatterjee et al., "Idiotype vaccines against human T cell acute lymphoblastic leukemia" *J.Immunol.* (1987) 139(4):1354–1360.
Bhattacharya–Chatterjee et al., "Idiotype vaccines against human T cell leukemia" *J.Immunol.* (1988) 141(4):1398–1403.
Bhattacharya–Chatterjee et al., "Idiotype matching: a network antigen idiotype is expressed in sera of colon cancer patients" *Vaccine Research* (1993) 2(4):283–290.
Bhattacharya–Chatterjee et al., "Murine anti–idiotype (Id)monoclonal antibody (mAb) breaks tolerance and induces a specific antibody response to carcinoembryonic (CEA) in coloretal cancer (CRC) patients" *FASEB J.* (1994) 8(4):A200 (Abstract No. 1156).
Bhattacharya–Chatterjee et al., "Anti–idiotype monoclonal antibodies as vaccines for human cancer" *Intern. Rev. Immunol.* (1991) 7:289–302.
Bhattacharya–Chatterjee et al., "Active immunotherapy of colorectal cancer patients with murine monoclonal anti–idiotype antibody" *Proc. of Internatl. Cancer Congress* (1994) pp. 495–499. Original Abstract Submission Form also enclosed.
Bhattacharya–Chatterjee et al., "Syngeneic monoclonal anti– idiotype antibody related to human carcinoembryonic antigen" *Proc. of the Amer. Assoc. Cancer Res.* (1990) 31:279 (Abstract No. 1651).
Bhattacharya–Chatterjee et al., "Idiotype matching: level of expression of a network antigen idiotype in colon cancer patients' SERA" *FASEB J.* (1991) 5(5):A1356 (Abstract No. 5713).
Chakraborty et al., "Murine monoclonal anti–idiotype antibody induces a specific antibody response to human carcinoembryonic antigen (CEA) in cynomolgus monkeys" *FASEB J.* (1994) 8(4):A504 (Abstract No. 2917).
Chakraborty et al., "Preclinical evaluation in nonhuman primates of an anti–idiotypic antibody that mimicks the carcinoembryonic antigen" *J.Immunother.* (1995) 18(2):95–103.
Chatterjee et al., "Antiidiotype (Ab2) vaccine therapy for cutaneous T–cell lymphoma" *Ann N.Y. Acad. Sci.* (1993) 690:376–377.
Cheresh et al., "Biosynthesis and expression of the disialoganglioside $G_{D2}$, a relevant target antigen on small cell lung carcinoma for monoclonal antibody–mediated cytolysis" *Cancer Research* (1986) 46:5112–5118.
Foon et al., "Immune response to the carcinoembryonic antigen in patients treated with an anti–idiotype antibody vaccine" *J. Clin. Invest.* (1995) 96:334–342.
Dialog Abstract of Foon et al., "Anti–idiotype vaccine (3H1) that mimics the carcinoembryonic antigen (CEA) as adjuvant treatment" *Proc. Annu. Meet. Am. Soc. Clin. Oncol.* (1996). One page total.
Goldenberg, "Monoclonal antibodies in cancer detection and therapy" *Am. J. Med.* (1993) 94(3):297–312.

(List continued on next page.)

*Primary Examiner*—Karen M. Hauda
*Assistant Examiner*—Anne Marie S. Beckerleg
(74) *Attorney, Agent, or Firm*—Morrison & Foerster LLP

(57) ABSTRACT

The present invention provides methods of delaying development of CEA-associated tumors using the anti-idiotype antibody 3H1, particularly in high-risk individuals.

57 Claims, 13 Drawing Sheets

OTHER PUBLICATIONS

Hansen et al., "Characterization of second-generation monoclonal antibodies against carcinoembryonic antigen" *Cancer* (1993) 71(11):3478–3485.

Hansen et al., "Solving the problem of antibody interference in commercial "sandwich" –type immunoassays of carcinoembryonic antigen" *Clin. Chem.* (1989) 35(1):146–151.

Herlyn et al., "Anti–idiotype immunization of cancer patients: Modulation of the immune response", *Proc. Natl. Acad. Sci. USA* (1987) 84:8055–8059.

Hinoda et al., "Internal image–bearing anti–idiotypic monoclonal antibodies" *Tumor. Biol.* (1995) 16:48–55.

Honjo et al., "Cloning and complete nucleotide sequence of mouse immunoglobulin γ1 chain gene" *Cell* (1979) 18:559–568.

Irvine et al., "Induction of delayed–type hypersensitivity responses by monoclonal anti–idiotypic antibodies to tumor cells expressing carcinoembryonic antigen and tumor–associated glycoprotein–72" *Cancer Immunol. Immunother.* (1993) 36:281–292.

Jerne, N.K., "Towards a network theory of the immune system" *Ann. Immunol.* (1974) 125:373–389.

Khazaeli et al., "Phase I trial of multiple large doses of murine monoclonal antibody CO17–1A.II Pharmacokinetics and immune response" *J.Natl. Cancer Inst.* (1988) 80(12):937–942.

Kuroki et al., "Biochemical characterization of 25 distinct carcinoembryonic antigen (CEA) epitopes recognized by 57 monoclonal antibodies and categorized into seven groups in terms of domain structure of the CEA molecule" *Hybridoma* (1992) 11(4):391–407.

Laemmli, "Cleavage of structural proteins during the assembly of the head of bacteriophage T4" *Nature* (1970) 227:680–685.

Lindenmann, "Speculations on idiotypes and homobodies" *Ann. Immunol.* (1973) 124:171–184.

Losman et al., "Mimicry of a carcinoembryonic antigen epitope by a rat monoclonal anti–idiotype antibody" *Int. J. Cancer* (1994) 56:580–584.

McBride et al., "Induction of tolerance to a murine fibrosarcoma in two zones of dosage—the involvement of suppressor cells" *Br. J. Cancer* (1986) 53(6):707–711.

Mittelman et al., "Human high molecular weight melanoma–associated antigen (HMW–MAA) mimicry by mouse anti–idiotypic monoclonal antibody MK2:23: Induction of humoral anti–HMW–MAA immunity and prolongation of survival in patients with stage IV melanoma" *Proc. Natl. Acad. Sci. USA* (1992) 89(2):466–470.

Mukerjee et al., "Generation of monoclonal anti–idiotype antibodies (Ab3) that recognize human carcinoembryonic antigen (CEA)" *FASEB J.* (1990) 4:A1951 (Abstract No. 1497).

Oikawa et al., "Primary structure of human carcinoembryonic antigen (CEA) deduced from cDNA sequence" *Biochem. Biophys. Res. Comm.* (1987) 142(2):511–518.

Pervin et al., "Induction of antitumor immunity by an anti–idiotype antibody mimicking carcinoembryonic antigen" *Cancer Research* (1997) 57(4):728–734.

Dialog record of Pervin et al., "Proliferation of T–cells from colon cancer patients by peptides based on the structure of an anti–idiotype antibody mimicking CEA" *Proceedings of the Amer. Assoc. for Cancer Research* (1996) Washington, D.C.. A copy of the original AACR abstract form is also enclosed. Two pages total.

*Remington's Pharmaceutical Sciences,* Alfonso R. Gennaro, ed., 18th edition., 1990. A copy of the cover page and table of contents are included herewith.

Robbins et al., "Transduction and expression of the human carcinoembyronic antigen gene in a murine colon carcinoma cell line" *Cancer Res.* (1991) 51(14):3657–3662.

Solin et al., "Immunoglobulin constant kappa gene alleles in twelve strains of mice" *Immunogenetics* (1993) 37:401–407.

Takahashi et al., "Induction of CD8 cytotoxic T cells by immunization with purified HIV–1 envelope protein in ISCOMs" *Nature* (1990) 344:873–875.

Foon et al. (Jul. 1995) J. Clin. Invest. vol. 96, 334–342.*

Hinoda et al. (1995) Tumor Biol. vol. 16, 48–55.*

Herlyn et al. (Nov. 1987) Proc. Natl. Acad. Sci., vol. 84, 8055–8059.*

Mittelman et al. (Jan. 1994) Cancer Research, vol. 54, 415–421.*

Orkin et al. (Dec. 1995) NIH Report and Recommendations of the Panel to Assess the NIH Investment in Research on Gene Therapy.*

* cited by examiner

3H1L SEQ

TCA TAT GGA TTA CTA GTC GAC

ATG GTA TCC ACA GCT CAG TTC CTT GGT ATC TTG TTG CTC TGG TTT CCA GGT

ATC AAA TCT GAC ATC AAG ATG ACC CAG TCT CCA TCT TCC ATG TAT GCA TCT

CTA GGA GAG AGA GTC ACG ATC ACT TGC AAG GCG AGT CAG GAC ATT AAT GGT

TAT TTA AAT TGG TTC CAA CAA GAA CCA GGG AAA TCT CCT AAG ACC CTG ATC

TAT CGT GCA AAT AGA TTG ATA GAT GGG GTC CCA TCA AGG TTC AGT GGC AGT

GGA TCT GGG CAA GTT TAC TCT CTC ACC ATC AGC AGC CTG GAA TTT CCG TGG ATG TTC GGT

ATG GGA ACT TAT TAT TGT CTA CAG TTT GAT GAG TTT CCG TGG ATG TTC GGT

GGA GGC ACC AAG CTG GAA ATC AAA CGG GCT GAT GCT GCA CCA ACT GTC TCC

ATC TTC CCA CCA TCC AGT

Fig. 6A

3H1L.pep

MVSTAQFLGILLLWFPGIKS

DIKMTQSPSSMYASLGERVTITC

KASQDINGYLN

WFQQEPGKSPKTLIY

RANRLID

GVPSRFSGSGSGQVYSLTISSLEYEDMGTYYC

LQFDEFPWMFGGGTKLEIK

RADAAPTVSIFPPSS

Fig. 6B

3H1H.SEQ

AGTCATATGGATTGGGAATTC

ATG GAA TGG AGC TGG GTC ATT CTC TTC CTC CTG TCA GGA ACT GCA GGT

GTC CAC TCT GAG GTC CAG CTG CAA CAG TCT GGA CCT GAG CTG GTG AAG CCT

GGA GCT TCA CTG AAG ATT TCC TGC GAG GCT TCT GGT TAC TCA CTC ACT GCC

TAC ACC ATG AAC TGG GTG AAG CAG AGC CAT GGA AAG AGC CTT GAG TGG GTT

GGG CTG ATT AAT CCT TTC AGT GGT GAT ACT AAC TAC AGC CAG AAA TTC ACG

GGC AAG GCC ACA TTA ACT GTA GAC AGG TCA TCC AGC ACA GCC TAC ATG GAG

CTC CTC AGT CTG ACA TCT GAG GAC TCT GCA GTC TAT TAC TGT GTC ATT ACT

CCG GTT CCC TAC TGG TAC TTC GAT GTC TGG GGC GCA GGG ACC ACG GTC ACC

GTC TCC TCA GCC AAA ACG ACA CCC CCA TCC GTC TAT

MEWSWVILFLLSGTAGVHS

EVQLQQSGPELVKPGASLKISCEASGYSLT

AYTMN

WVKQSHGKSLEWVG

LINPFSGDTNYSQKFTG

KATLTVDRSSSTAYMELLSLTSEDSAVYYCVI

TPVPYWYFDV

WGAGTTVTVSS

AKTTPPSVY

Fig. 7B

METHODS OF DELAYING DEVELOPMENT OF CEA-ASSOCIATED TUMORS USING ANTI-IDIOTYPE ANTIBODY 3H1

CROSS-REFERENCE TO RELATED APPLICATIONS

This application claims the benefit of U.S. Provisional Application No. 60/044,455 formerly U.S. Ser. No. 08/631,085, filed Apr. 12, 1996.

STATEMENT OF RIGHTS TO INVENTIONS MADE UNDER FEDERALLY SPONSORED RESEARCH (Not Applicable)

FIELD OF THE INVENTION

This invention relates to uses of anti-idiotype antibodies. More particularly, it relates to methods of treatment using anti-idiotype antibody 3H1, in which administration of 3H1 delays CEA-associated tumor development.

BACKGROUND OF THE INVENTION

In spite of extensive medical research and numerous advances, cancer remains the second leading cause of death in the United States. Colorectal cancer is the third most common cancer and the second leading cause of cancer deaths. While the traditional modes of therapy, such as surgery, radiotherapy and chemotherapy, are widely used and are in many instances successful, the still existing high death rate from cancers such as colorectal compels the need for alternative or additional modes of therapy.

Even if a patient responds to traditional modes of therapy, there is often a significant risk of recurrence of the disease. This is especially true if the disease has spread when diagnosed. Even after "successful" treatment, in which a remission is observed, a patient can have high risk of recurrence, and can only "watch and wait." There are presently no further courses of action to delay or prevent recurrence.

One approach to cancer therapy has been immunotherapy. However, immunotherapy of human cancer using tumor cells or tumor-derived vaccines has been disappointing for several reasons. It has been consistently difficult to obtain large quantities or purified tumor-associated antigens which are often chemically ill-defined and difficult to purify. In addition, there remains the problem of immunobiological response potential against tumor antigens, or in other words, the question of whether a cancer patient can effectively mount an immune response against his or her tumor. Tumor-associated antigens (TAA) are often a part of "self" and usually evoke a very poor immune response in a tumor-bearing host due to tolerance to the antigens, such as T cell-mediated suppression. Moreover, cancer patients tend to be immunosuppressed and only respond to certain T-dependent antigens.

Immunobiologists have learned that a poor antigen (in terms of eliciting an immune response) can be turned into a strong antigen by changing the molecular environment. Changes of hapten carrier allow T cell helper cells to become active, making the overall immune response stronger. Thus, changing the carrier can also turn a tolerogenic antigen into an effective antigen. McBride et al. (1986) *Br. J. Cancer* 53:707. Often the immunological status of a cancer patient is suppressed such that the patient is only able to respond to certain T-dependent antigens and not to other antigen forms. From these considerations, it would make sense to introduce molecular changes into the tumor associated antigens before using them as vaccines. Unfortunately, this is impossible to accomplish for most tumor antigens, because they are not well defined and are very hard to purify.

The network hypothesis of Lindenmann ((1973) *Ann. Immunol.* 124:171–184) and Jerne ((1974) *Ann. Immunol.* 125:373–389) offers an elegant approach to transform epitope structures into idiotypic determinants expressed on the surface of antibodies. According to the network concept, immunization with a given tumor-associated antigen will generate production of antibodies against this tumor-associated antigen, termed Ab1; this Ab1 is then used to generate a series of anti-idiotype antibodies against the Ab1, termed Ab2. Some of these Ab2 molecules can effectively mimic the three-dimensional structure of the tumor-associated antigen identified by the Ab1. These particular anti-idiotypes called Ab2β fit into the paratopes of Ab1, and express the internal image of the tumor-associated antigen. The Ab2β can induce specific immune responses similar to those induced by the original tumor-associated antigen and can, therefore, be used as surrogate tumor-associated antigens. Immunization with Ab2β can lead to the generation of anti-anti-idiotype antibodies (Ab3) that recognize the corresponding original tumor-associated antigen identified by Ab1. Because of this Ab1-like reactivity, the Ab3 is also called Ab1' to indicate that it might differ in its other idiotopes from Ab1.

A potentially promising approach to cancer treatment is immunotherapy employing anti-idiotype antibodies. In this form of therapy, an antibody mimicking an epitope of a tumor-associated protein is administered in an effort to stimulate the patient's immune system against the tumor, via the tumor-associated protein. WO 91/11465 describes methods of stimulating an immune response in a human against malignant cells or an infectious agent using primate anti-idiotype antibodies. However, not all anti-idiotype antibodies can be used in therapeutic regimens against tumors. First, only a fraction of antibodies raised against an Ab1 are limited in their reactivity to the paratope of Ab1 (i.e., are non-reactive against features shared with other potential antibodies in the host). Second, anti-idiotype antibodies are not necessarily immunogenic. Third, even if an anti-idiotype elicits an immune response, only a fraction of these immunogenic anti-idiotypes elicit an immune response against the tumor antigen and not against other antigens with less specificity. Moreover, since different cancers have widely varying molecular and clinical characteristics, it has been suggested that anti-idiotype therapy should be evaluated on a case by case basis, in terms of tumor origin and antigens expressed.

Anti-Id monoclonal antibodies structurally resembling tumor-associated antigens have been used as antigen substitutes in cancer patients. Herlyn et al. (1987) *Proc. Natl. Acad. Sci. U.S.A.* 84:8055–8059; Mittelmann et al. (1992) *Proc. Natl. Acad. Sci. U.S.A.* 89:466–470; Chatterjee et al. (1993) *Ann. N.Y. Acad. Sci.* 690:376–377. All of these studies were conducted with patients having advanced disease. Based on the observed immune response in at least some of the patients, it has been proposed that the anti-Id provides a partial analog of the tumor-associated antigen in an immunogenic context.

Carcinoembryonic antigen (CEA) is a 180,000-kiloDalton glycoprotein tumor-associated antigen present on endodermally-derived neoplasms of the gastrointestinal tract, such as colorectal and pancreatic cancer, as well as other adenocarcinomas such as breast and lung cancers. A majority of colorectal, gastric, pancreatic as well as breast and non-small cell lung carcinomas are associated with CEA. CEA is also found in the digestive organs of the human fetus. Circulating CEA can be detected in the great majority of patients with CEA-positive tumors. Specific monoclonal antibodies have been raised against CEA and some have been radiolabeled for diagnostic and clinical studies. Hansen et al. (1993) *Cancer* 71:3478–3485; Kuroki et al. (1992) *Hybridoma* 11:391–407; Goldenberg (1993) *Am. J. Med.* 94:297–312. As with most tumor-associated antigens which are seen as self-antigens by the immune system, cancer patients are immunologically "tolerant" to CEA, likely related to its oncofetal origin. This has rendered immunotherapy based on CEA virtually impossible. Studies to date on patients with CEA-positive tumors have not demonstrated the ability to generate immunity to CEA.

CEA nonetheless is an excellent tumor-associated antigen for active immunotherapy with anti-idiotype antibody for several reasons. CEA is typically present at high levels on the tumor cell surface. CEA is also one of the most well-characterized antigens, as its gene sequence is known and its three dimensional structures have been identified. CEA is a member of the immunoglobulin supergene family located on chromosome 19 which is thought to be involved in cell-cell interactions.

Inasmuch as some of the epitopes on CEA are shared by normal tissues, immunization with intact CEA molecule might trigger potentially harmful autoimmune reactions. An immune reaction against a tumor associated epitope, on the other hand, would be desirable. A number of investigators have generated anti-idiotype antibodies in rats, mice, baboons and humans that mimic CEA. See, e.g., Hinoda et al. (1995) *Tumor Biol.* 16:48–55; Losman et al. (1994) *Int. J. Cancer* 56:580–584; Irvine et al. (1993) *Cancer Immunol. Immunother.* 36:281–292. However, given the size of CEA (and likely numerous epitopes), and the fact that CEA is expressed on some normal tissues, it was not known whether anti-idiotype antibodies would be effective in eliciting an anti-CEA response that effects anti-tumor immunity.

CEA-associated tumors, such as carcinomas of the gastrointestinal tract, are often not curable by standard therapies. Even if a patient responds to traditional therapy, there is often a significant risk of recurrence. Thus, new therapeutic approaches for this disease are needed. The present invention overcomes the deficiencies in the prior art by providing methods of treatment for CEA-associated tumors using monoclonal anti-idiotype antibody (3H1) which escapes immune tolerance and induces an anti-CEA immune response.

All references cited herein are incorporated by reference in their entirety.

SUMMARY OF THE INVENTION

The present invention is directed to therapeutic uses of the anti-idiotype antibody 3H1.

Accordingly, one aspect of the invention is methods of delaying development of CEA-associated tumors an individual having a low tumor burden, particularly high risk individuals. These methods include administration of an effective amount of anti-idiotype antibody 3H1 to the individual. In another aspect, the invention further includes administration of 3H1 with an adjuvant.

In another aspect, methods are provided for treatment of a CEA-associated tumor in an individual with a low tumor burden which entail administering an effective amount of 3H1 to the individual.

In another aspect, methods are provided for treatment of a CEA-associated tumor in an individual having a low tumor burden and having a level of circulating CEA less than about 50 ng/ml, which entail administration of an effective amount of 3H1 to the individual.

In another aspect, 3H1 is used to treat a CEA-associated tumor of colon or colorectal origin. These methods include administration of an effective amount of 5-fluorouracil, levamisole hydrochloride or leucovorin calcium, and an effective amount of 3H1 to an individual.

BRIEF DESCRIPTION OF THE DRAWINGS

FIG. 1(A) depicts an assay of anti-3H1 antibody; FIG. 1(B) depicts an assay of anti-CEA antibody; FIGS. 1(C) and (D) depict T cell proliferative response (solid bar denotes CEA; open bar denotes 3H1). N indicates PBS vaccinated mice.

FIGS. 2(A–C) is a series of graphs depicting the increased survival after tumor challenge in mice inoculated with 3H1. Survival was measured after six immunizations with 3H1. Circles denote challenge with MC38 (CEA negative) cells; squares denote challenge with MC38cea (CEA positive) cells.

FIGS. 6(A+B) depicts the cDNA sequence (SEQ ID NO:3; FIG. 6A) and the amino acid sequence (SEQ ID NO:4; FIG. 6B) of the light chain variable region of 3H1 and adjoining residues.

FIGS. 7(A+B) depicts the cDNA sequence (SEQ ID NO:5; FIG. 7A); and the amino acid sequence (SEQ ID NO:6; FIG. 7B) of the heavy chain variable region of 3H1 and adjoining residues.

FIG. 8(A) depicts an assay of anti-3H1 antibody; In FIG. 8(A), Ab2-C1 denotes control antibody 1A7; Ab2-C2 denotes control plates coated with 3H1 but serum samples were from mice immunized 5 times with 1A7-KLH conjugate. Other lines in the graph indicate different numbers of immunizations (3×; 5×; 6×; 7×) and pre-immune serum. In FIG. 8(B), absorbance was measured before and after 3 ("3×"), 5 ("5×"), and 7 ("7×") weekly injections.

FIGS. 9(A)–(C) show incubation of MC-38-cea cells (A, sera from mice before and after six immunizations with 3H1-KLH conjugate; B, PBS and monoclonal anti-CEA antibody 8019; C, sera from mice before and after six immunizations with isotype-matched unrelated anti-idiotype antibody 1A7-KLH. FIGS. 9(D)–(F) show incubation of MC-38 cells (D, before and after six immunizations with 3H1-KLH conjugate; E, PBS and 8019; F, before and after six immunizations with 1A7-KLH).

DETAILED DESCRIPTION OF THE INVENTION

Figure 1A:
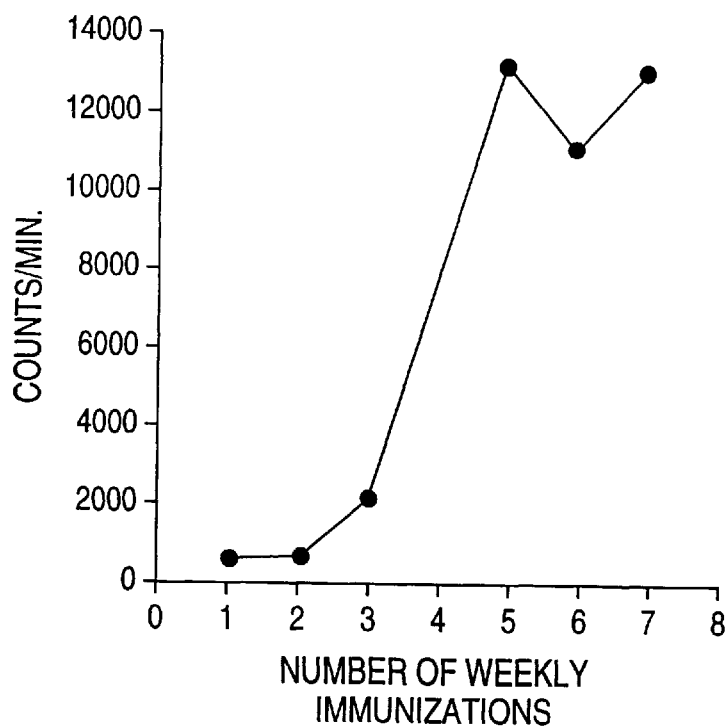
FIGS. 1(A)–(D) are graphs depicting the generation of an immune response in mice inoculated with 3H1.

We have discovered that administration of 3H1 increases survival in mice having CEA-positive tumors and protects mice from a tumor challenge. We have also found that administration of the anti-idiotype antibody 3H1 in humans who have had CEA-associated tumors successfully treated (i.e., no detectable metastasis or disease) elicits a CEA-specific immune response. Importantly, we have also discovered that administration of 3H1 to individuals having low tumor burden who are at high risk of recurrence of CEA-associated tumors remain asymptomatic longer than would be statistically expected. In particular, one patient with virtually a 100% risk of recurrence within six months remained asymptomatic for over twenty months after receiving 3H1. We believe that administration of 3H1 can reduce the risk of CEA-associated tumor occurrence, particularly in high risk individuals in the adjuvant setting.

3H1 is a murine monoclonal anti-idiotype (Id) antibody (Ab2) which induces a specific immune response against a distinct and specific epitope of carcinoembryonic antigen (CEA), a tumor-associated antigen. This epitope is unique to CEA and is not present on other CEA-related lower molecular weight members of this family which are also found on normal tissues. The antigenic determinant as defined by the monoclonal antibody 8019 (Ab1) against which 3H1 was raised is absent on normal adult tissues as evidenced by immunoperoxidase staining and hematopoietic analysis. The generation and characterization of 3H1 has been described in commonly owned patent application Ser. No. 08/579,940, as well as the DNA sequences encoding the variable regions of 3H1 (light and heavy chains). A hybridoma that produces 3H1 has been deposited with the American Type Culture Collection (ATCC), 12301 Parklawn Drive, Rockville, Md., U.S.A. 20852 on Dec. 15, 1995, under the provisions of the Budapest Treaty for the International Recognition of the Deposit of Microorganisms for the Purposes of Patent Procedure. It was accorded Accession Number HB 12003.

In a previous Phase I clinical trial, 12 colorectal cancer patients having advanced CEA-associated disease (who had failed all previous therapy and still had high tumor burden) were administered 3H1. Bhattacharya-Chatterjee et al. (1994) XVI Internat'l Cancer Congress pp. 495–498. Nine of the 12 patients developed high titers of specific anti-anti-Id (Ab3) antibodies that were capable of inhibiting binding of Ab1 to Ab2 or CEA. All nine of these patients also generated specific anti-CEA antibodies which reacted with purified CEA and showed the identical immunostaining patterns as Ab1 on autologous and allogeneic colonic tumors. Furthermore, 7 of the 12 patients demonstrated Id-specific T cell proliferative responses. Four of these seven patients also showed T cell proliferation in the presence of CEA. Toxicity was minimal for all 12 patients. However, all of these patients displayed normal disease progression.

Definitions

As used herein, the terms "3H1," "3H1 antibody" and "3H1 monoclonal anti-idiotype antibody" are used interchangeably to refer to an anti-idiotype antibody (Ab2) which contains an epitope that at least partially resembles a distinct and specific epitope of the 180,000 M.W. carcinoembryonic antigen (CEA) primarily expressed in high density by human pancreatic and colonic tumor cells. The generation and characterization of 3H1 is described in commonly owned patent application Ser. No. 08/579,940. Different biological functions are associated with 3H1, including, but not limited to, binding to Ab1 (8019) and/or Ab3 and an ability to induce an immune response (humoral and/or cellular) against CEA in mice, rabbits, monkeys, and humans with advanced CEA-associated disease, particularly CEA-associated tumors, as well as humans with a history of CEA-associated disease but no detectable disease.

A "CEA-associated tumor" is one that contains a CEA antigen, especially expressed on the tumor cell surface. Methods of detecting CEA are known in the art and examples are described herein.

As used herein, "treatment" is an approach for obtaining beneficial or desired clinical results. For purposes of this invention, beneficial or desired clinical results include, but are not limited to, one or more of the following: alleviation of symptoms, diminishment of extent of disease, stabilized (i.e., not worsening) state of disease, preventing spread (i.e., metastasis) of disease, preventing occurrence or recurrence of disease, delay or slowing of disease progression, amelioration of the disease state, and remission (whether partial or total). Also encompassed by "treatment" is a reduction of pathological consequences of a CEA-associated tumor(s).

As used herein, "delaying" development of a CEA-associated tumor(s) means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of CEA-associated tumor(s) is a method that reduces probability of disease development in a given time frame and/or reduces extent of the disease in a given time frame, when compared to not using the method. Such comparisons are typically based on clinical studies, using a statistically significant number of subjects.

"Development" of CEA-associated tumor(s) means progression of the tumor(s). Tumor development can be detectable using standard clinical techniques as described herein. However, development also refers to disease progression that may be undetectable. For purposes of this invention, progression refers to the biological course of the disease state, in this case (i.e., CEA-associated tumors) cell division and/or metastasis of the CEA-associated tumor. "Development" includes occurrence, recurrence, and onset. As used herein "onset" or "occurrence" of CEA-associated disease includes initial onset and and/or recurrence.

As used herein, "low tumor burden" means that an individual does not have advanced CEA-associated tumor(s). "Advanced" CEA-associated tumor(s) means that there is detectable metastasis, that is, detectable tumor masses at sites other than the primary site of the tumor. Tumor masses are preferably detected by imaging techniques known in the art such as X-ray, CT scan, or MRI. "Advanced" disease does not include lymph node involvement. As the term indicates, "low tumor burden" indicates a lesser extent of disease than the maximum, or end-stage levels that have been described for CEA-associated tumors. It is understood that "low tumor burden" also includes no detectable tumor. Examples of low tumor burden categories are provided below.

As used herein, a "high risk" individual is an individual who is at major risk of development of CEA-associated tumors. A "high risk" individual may or may not have detectable disease, and may or may not have displayed detectable disease prior to the treatment methods described herein. "High risk" denotes that an individual has one or more so-called risk factors, which are measurable parameters that correlate with development of CEA-associated tumors. An individual having one or more of these risk factors has a higher probability of developing CEA-associated tumors than an individual without these risk factor(s). These risk factors include, but are not limited to, age, sex, race, diet, history of previous disease, presence of precursor disease, genetic (i.e., hereditary) considerations, and environmental exposure. Examples (i.e., categories) of high-risk groups are discussed below.

Depending on the basis and context of assessment of high risk, the time frame within which probability of disease or tumor development, progression, and/or onset would more likely than not occur would vary. For instance, with breast, colorectal, and/or adenocarcinoma high risk patients in the adjuvant setting, the risk of occurrence is typically measured within one to two years. For patients who display precursor disease, the risk of occurrence can be measured in a longer time frame. For an individual who is considered high risk due to, for example, genetic or hereditary considerations, the risk of occurrence can be measured in an even longer time frame, including the expected lifetime of the individual.

An individual with "low risk" is one who is not considered "high risk".

"Adjuvant setting" refers to a clinical setting in which an individual has had a history of CEA-associated disease, particularly CEA-associated tumors, and has been responsive to therapy. The prior therapy can have included, but is not limited to, surgical resection, radiotherapy, and chemotherapy. As a result of this prior therapy, these individuals have no clinically measurable tumor. However, because of their history of CEA-associated disease, these individuals are considered at risk of development of the disease. Treatment or administration in the "adjuvant setting" refers to a subsequent mode of treatment. The degree of risk (i.e., whether an individual in the adjuvant setting is considered "high risk" or "low risk") depends upon several factors, most usually the extent of disease when first treated.

As used herein, "adjuvant setting" is distinguished from an "adjuvant", which refers to a chemical or biological agent in a pharmaceutical preparation given in combination with an agent (such as an antibody, polynucleotide or polypeptide) to enhance its immunogenicity. Examples of adjuvants are described herein.

A "neo-adjuvant setting" refers to the period after diagnosis but before initiation of treatment modalities other than administration of 3H1. For example, if an individual is diagnosed as having a CEA-associated tumor, such as colorectal, for which surgery is indicated, administration of 3H1 in a neo-adjuvant setting means that administration of 3H1 commences before surgery.

An "effective amount" is an amount sufficient to effect beneficial or desired clinical results. An effective amount can be administered in one or more administrations. For purposes of this invention, an effective amount of 3H1 is an amount of 3H1 that is sufficient to ameliorate, stabilize, or delay the development of the CEA-associated disease state, particularly CEA-associated tumors. Detection and measurement of these indicators of efficacy are discussed below.

An "individual" is a vertebrate, preferably mammal, more preferably human. Mammals include, but are not limited to, farm animals, sport animals, and pets.

Embodiments of the Invention

In one embodiment, the invention provides methods delaying development of a CEA-associated tumor(s) in which an effective amount of 3H1 is administered to an individual having a low tumor burden. Examples of CEA-associated tumors include, but are not limited to, carcinomas of the gastrointestinal tract (including colorectal cancer), other adenocarcinomas such as breast, lung (non small cell) cancer, biliary (including biliary tree) cancer and gynecological cancer. Methods of detecting CEA-associated tumors are known in the art, including standard immunoassay techniques. As an example, CEA-associated tumors can be detected by standard immunohistologic examination of affected tissue, using, for example, 8019 as the primary antibody in an indirect immunofluorescence assay.

In one embodiment, the invention encompasses administration of 3H1 to a high risk individual having a low tumor burden. As discussed above, a high risk individual displays one or more risk factors that correlate with CEA-associated tumor development. High (i.e., increased) risk may be indicated, for example, on the basis of an individual's genotype (for example, familial polyps), increased expression of tumor-associated genes or decreased expression of tumor suppressor genes, presence of precursor disease (such as polyps), a family history of CEA-associated cancer, a history of exposure to an environmental substance or form of radiation which is known or suspected of being carcinogenic or teratogenic (particularly suspected of causing CEA-associated tumors), exposure to a potentially carcinogenic pathogen such as a retrovirus, or a history of other types of cancer or other types of abnormal or unregulated tissue growth. Also included as high risk are individuals suspected of having a CEA positive tumor based on a positive test for anti-CEA immunological reactivity.

Because all risk factors for developing CEA-associated tumors are not known, and the interplay among these factors (in terms of overall risk) are not fully understood, it is clear to one skilled in the art that individuals suitable for administration of 3H1 for purposes of this invention can have clinical features in common, and that individuals not falling clearly in the categories described above can nonetheless be considered suitable candidates for administration of 3H1. A skilled clinician can make an empirical determination whether an individual is suitable for 3H1 treatment. For example, an individual with a familial (i.e., genetic) history of colorectal cancer could be considered "high risk", even though no previous disease in this individual has been observed. In this context, administration of 3H1 to such an individual could result in delay of occurrence of disease, to the extent that the individual does not develop the disease within his or her lifetime (or develops it later than would have been expected). Another example is an individual who is being treated using traditional modes of therapy, and who is showing clinical responsiveness to the therapy (i.e., remission). Such an individual may be adjudged as "high risk", even though the initial course of therapy is not yet completed, due to projection of clinical progress by the clinician, and can be a suitable candidate for receiving 3H1 before completion of the initial therapy. The clinician, as one skilled in the art, has discretion to determine whether treatment using 3H1 may be indicated.

It is also evident that administration of 3H1 may be indicated even if an individual is not adjudged to be high risk (i.e., is "low risk") according to concurrent clinical risk assessment criteria. For instance, an individual who has been successfully treated and is not considered high risk (due, for example, to the lack of detectable invasive disease at the time of diagnosis) may nonetheless be a candidate for receiving 3H1 as a precautionary measure, especially considering the lack of contraindications and lack of undesirable side effects so far observed from 3H1. Thus, the risk of disease progression may be lowered even further by administration of 3H1. As another example, an individual may believe that he or she is at risk of disease development, and may decide that receiving 3H1 would reduce this risk. Also suitable are individuals with supernormal levels of circulating CEA and/or supernormal levels of CEA expression. The circulating level of CEA can be determined by standard immunoassay ELISA) techniques which are commercially available (Hybritech). Levels of CEA expression can be determined by, for example, immunohistologic examination of affected tissue, using, for example, 8019 as the primary antibody in an indirect immunofluoresce assay.

As used herein, "supernormal" levels of CEA are greater than about 3 ng/ml. As is evident to one of skill in the art, the levels of circulating CEA can vary among laboratories (and depending upon the method and/or commercial kit used). Thus, supernormal levels of CEA can be greater than about 1 ng/ml to greater than about 5 ng/ml.

In another embodiment of the present invention, 3H1 is administered to a high risk individual in the adjuvant setting. Factors typical as indicating individuals of high risk in the adjuvant setting are invasion by the tumor into neighboring tissues (i.e., extensive disease), and/or lymph node involvement. Examples of high risk individuals in the adjuvant setting include, but are not limited to, (a) patients with Stage II or Stage IIIA adenocarcinoma of the lung with positive lymph nodes who have had their tumor resected (these patients have a 60–80% relapse rate in the first 2 years); (b) patients with breast cancer who have positive lymph nodes in preferably at least 5, more preferably at least 10 (70–80% relapse rate in the first 2 years for those with at least 10 positive lymph nodes); and (c) patients with colon cancer with at least 4 positive lymph nodes (70–80% relapse rate in the first 2 years). Another example of a high risk individual in the adjuvant setting is an individual having a gastric CEA-associated tumor that has been resected, including, but not limited to, pancreatic, gastric and biliary (including biliary tree) cancers.

In another embodiment, 3H1 is administered in a neo-adjuvant setting. It is understood that, for purposes of this invention, an individual in a neo-adjuvant setting has a low tumor burden.

Another example of an individual suitable for 3H1 therapy as described in this invention is an individual with low tumor burden. Thus, the present invention encompasses methods of treating CEA-associated tumors in an individual having a low tumor burden comprising administering an effective amount of 3H1. As defined above, a "low" tumor burden means that the disease is not considered advanced. For example, a low tumor burden can be disease in partial or complete remission as adjudged by a clinical practitioner. "Low" tumor burden can also arise by a reduction of tumor burden of advanced disease such that the extent of disease is no longer considered advanced. Other examples of low tumor burden include disease contained to limited lymph node involvement. For these individuals, circulating CEA levels are usually less than or equal to about 50 ng/ml, preferably less than or equal to about 10 ng/ml, more preferably less than or equal to about 5 ng/ml, even more preferably less than or equal to about 3 ng/ml. An individual with a low tumor burden can be further classified as "high risk" or "low risk," depending on the individual's clinical history.

The invention also includes methods of treatment using 3H1 for individuals having residual disease, particularly minimal residual disease. "Residual" disease is any CEA-associated disease, particularly CEA-associated tumor(s) remaining after therapy but which is undetectable. Thus, "residual disease" refers to the likely presence of disease that can develop into detectable disease, and refers to a clinical prognosis and/or assumption made in an adjuvant setting. Depending on the type of CEA-associated tumor and, for example, the extent of disease upon diagnosis, an individual can be adjudged to have residual disease, even though no detectable disease is present. For example, an individual with resectable lung adenocarcinoma has residual disease after surgery (i.e., resection), even if an apparent complete remission has occurred. Similarly, an individual with colorectal cancer can have residual disease after chemotherapy. Alternatively, an individual who is currently undergoing therapy for a CEA-associated tumor also has "residual" disease. It is understood that, as used herein, "residual" disease does not include advanced disease.

The invention also encompasses methods of reducing risk of occurrence of CEA-associated disease, particularly CEA-associated tumors. In these methods, an effective amount of 3H1 is administered to an individual at risk for developing CEA-associated disease. "Reducing risk of occurrence" means that the risk of occurrence and/or reoccurrence of CEA-associated disease is lower in individuals receiving 3H1 than those individuals (having the same risk of occurrence) who do not. An individual "at risk" for developing CEA-associated disease can be high risk or low risk, depending on the clinical and genetic history and status of the individual.

The invention also encompasses methods of treatment of a CEA-associated tumor in an individual having a low tumor burden and who has a circulating level of CEA less than about 50 ng/ml. These methods entail administration of an effective amount of 3H1 to the individual. Preferably, the individual has a circulating level of CEA less than about 30 ng/ml, more preferably less than about 25 ng/ml, still more preferably less than about 20 ng/ml, even more preferably less than about 15 ng/ml, even more preferably less than about 10 ng/ml, even more preferably less than about 5 ng/ml. Methods of measuring levels of circulating CEA are known in the art and some are described herein (see, e.g., Example 4).

In another embodiment, the invention provides methods of treating a CEA-associated tumor, particularly adenocarcinoma, particularly adenocarcinoma of the colon and/or rectum, which include administration of fluorouracil (5-FU) with levamisole hydrochloride or leucovorin calcium, and 3H1. We believe that 5-FU and levamisole or leucovorin may act synergistically with 3H1 to enhance the immune response. 5-FU with levamisole or leucovorin are treatments currently known in the art, and for purposes of this invention, they are administered according to accepted clinical protocols (described in more detail below).

For all of the above-described embodiments of the present invention, 3H1 can be prepared, administered, and monitored as described in the following sections.

Preparation and Administration of Anti-idiotype Antibody 3H1

All embodiments of this invention entail administration of an effective amount of 3H1.

3H1 can be obtained several ways. 3H1 can be produced from the hybridoma ATCC No. HB 12003 described herein. Methods of antibody isolation are well known in the art. See, for example, Harlow and Lane (1988) *Antibodies: A Laboratory Manual,* Cold Spring Harbor Laboratory, New York, and Sambrook et al. (1989) *Molecular Cloning: A Laboratory Manual,* Cold Spring Harbor Laboratory. The antibody can be obtained from the hybridoma via tissue culture or from mouse ascites. These techniques are known the art. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. Such methods are known in the art, and generally comprise injecting hybridoma cells into an immunologically naive histocompatible or immunotolerant mammal, especially a mouse. The mammal is optionally primed for ascites production by prior administration of a suitable composition; for example, Pristane. Preferably, 3H1 is purified from BALB/c ascites using recombinant protein G-agarose chromatography followed by Protein-A-CL-sepharose 4B chromatography.

Alternatively, 3H1 can be chemically synthesized using techniques known in the art, for example, using a commercially available automated peptide synthesizer such as those manufactured by Applied Biosystems, Inc. (Foster City, Calif.).

3H1 can also be obtained by employing routine recombinant methods such as described in Sambrook et al. (1989). For instance, a polynucleotide encoding either the 3H1 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 3H1 may be produced separately, and then combined by disulfide bond rearrangement. Alternatively, vectors with separate polynucleotides encoding each chain of 3H1, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The 3H1 thus produced in the host cell can be purified using standard techniques in the art.

Figure 5:
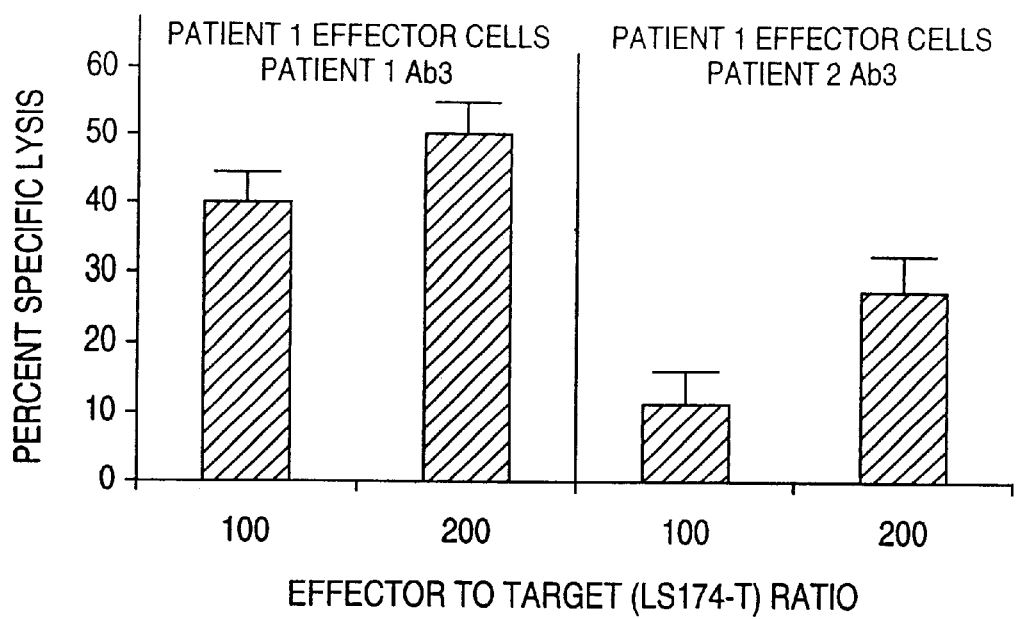
FIG. 5 is a bar graph depicting ADCC in the sera of 2 high risk patients receiving 3H1. In both halves of the graph, effector cells from patient #1 were used. Ab3 was from patient #1 (left side) or patient #2 (right side).

A polynucleotide encoding 3H1 for use in the production of 3H1 by any of these methods can in turn be obtained from the hybridoma producing 3H1, or be produced synthetically or recombinantly from the DNA sequences described in commonly owned patent application Ser. Nos. 08/579,940 and 08/579,916 using standard techniques in the art. FIG. 6A depicts the cDNA sequence of the light chain variable region of 3H1 (SEQ ID NO:3); FIG. 7A depicts the cDNA sequence of the heavy chain variable region of 3H1 (SEQ ID NO:5). The full sequences of the 11D10 light and heavy chain constant regions have not been determined, but are expected to be identical or nearly identical to those of other mouse immunoglobulin molecules. For the mouse kappa light chain constant region, four genetic allotypes encoding two protein allotypes have been published by Solin et al. (1993) *Immunogenetics* 37:401–407, which is hereby incorporated herein by reference. FIG. 1 of Solin et al. depicts mouse and rat immunoglobulin kappa chain gene sequences, comparing the sequences within the kappa chain constant region for different strains and highlighting allotypic differences. Included are kappa chain constant region sequences for BALB/c, PL, SJL, and *M. spretus.* Other naturally occurring allotypes are possible. The mouse $\gamma_1$ heavy chain constant region DNA sequence from newborn mice has been published by Honjo et al. (1979) *Cell* 18:559–568, which is hereby incorporated herein by reference. FIG. 5 of Honjo et al. shows the germ-line DNA sequence, along with the encoded protein sequence. Shown in the line above is another protein sequence obtained from the mouse myeloma MOPC 21. Other naturally occurring allotypes are possible.

Polynucleotides encoding 3H1 can also be derived from the amino acid sequence of 3H1, the variable regions of which are provided in FIG. 6 (light chain; SEQ ID NO:4) and FIG. 7 (heavy chain; SEQ ID NO:6). Given the amino acid sequence of 3H1, one of skill in the art can design polynucleotides encoding 3H1.

The 3H1 antibody is of the IgG1 mouse subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 3H1 may also be purified on affinity columns comprising the 8019 paratope; for example, in the form of a purified Ab1 or Ab3.

If 3H1 is to be administered to an individual, 3H1 is preferably at least 80% pure, more preferably at least 90% pure, even more preferably at least 95% pure, even more preferably at least 98% pure, as well as free of pyrogens and other contaminants. In this context, the percent purity is calculated as a weight percent of the total protein content of the preparation. Example 1 describes preparation of 3H1 for immunization.

Preferably, 3H1 is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences* (Alfonso R. Gennaro, ed., 18th edition, 1990).

Preferably, 3H1 is used with an adjuvant which enhances presentation of 3H1 or otherwise enhances the immune response against 3H1. Suitable adjuvants include aluminum hydroxide, alum, QS-21 (U.S. Pat. No. 5,057,540), DHEA (U.S. Pat. Nos. 5,407,684 and 5,077,284) and its derivatives (including salts) and precursors (e.g., DHEA-S), beta-2 microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives (e.g., DETOX™, and BCG (U.S. Pat. No. 4,726,947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873–875. For veterinary use and for production of antibodies in animals, mitogenic components of Freund's adjuvant can be used. The choice of an adjuvant will depend in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans. Preferably, alum-precipitated 3H1 is used. Preparation of aluminum hydroxide precipitated 3H1 is described in Example 1.

3H1 can be used in conjunction with other immunomodulators, such as, for example, interleukin 2 (IL-2), IL-4, IL-3, IL-12, GM-CSF, G-CSF, interferon and keyhole limpet hemocyanin (KLH).

3H1 can also be used in conjunction with other agents that serve to enhance and/or complement 3H1's effectiveness. Examples of such agents include, but are not limited to, peptides derived from CEA or 3H1. Preferred CEA and 3H1 peptides are those based on homology between 3H1 and CEA. In a preferred embodiment a peptide having the sequence IYRANRLIDGV (SEQ. I.D. NO:1) is administered with 3H1. This sequence is a portion of the 3H1 variable region and is homologous with part of the three homologous repetitive domains of CEA (Oikawa et al. (1987) Biochem. Biophys. Res. Comm. 142:511–518). In another embodiment, the peptide administered with 3H1 has the sequence PPAQYSWLIDGN (SEQ. I.D. NO:2). This peptide has an amino acid sequence contained within CEA. Other peptides can be suitable, including peptides that stimulate T cell activity.

Alternatively, 3H1 can be encapsulated in liposomes. Liposomes suitable for packaging polypeptides for delivery to cells are known in the art.

3H1 can be heat treated before administration and the heat treatment can be in the presence of adjuvant, for example, alum. For instance, 3H1 can be heated at about 40° to 80° C., preferably 45° C. to 60° C., for a period of about 5 minutes to 2 hours, preferably 15 minutes to 1 hour. Heat treatment is preferably at 45° C. for 30 minutes in a sterile vial in a water bath. The heat treatment can occur anytime before administration. Preferably, heat treatment is within 7 days of administration. Other heat treatment procedures can be used, as long as the desired activity of 3H1 is not significantly compromised. The heat-treated 3H1 is then administered as described herein.

For treatment using 3H1, an effective amount of 3H1 is administered to an individual parenterally, preferably intracutaneously. Other routes of administration include, but are not limited to, intramuscular and intradermal. 3H1 can also be administered indirectly, by treatment of cultured cells followed by introduction of these cultured cells into an individual. The routes of administration can also vary during a course of treatment. For example, an individual can receive 3H1 intravenously followed by interperitoneal administration.

The amount of 3H1 given to the individual will depend upon several factors, such as the condition of the individual, the weight of the individual, the nature of the disorder or disease being treated, the extent of disease, the route of administration, how many doses will be administered, and the desired objective. Preferably, the dose per administration will range from about 10 µg to 20 mg, preferably 200 µg to 15 mg, more preferably 500 µg to 10 mg, even more preferably 1 mg to about 4 mg, even more preferably 2 mg. Preferably, the dose is 2 mg of alum-precipitated 3H1.

The interval between administrations of 3H1 can vary and will depend upon the disorder being treated and the responsiveness of the individual. The 3H1 is preferably administered first as a priming dose followed by at least one boosting dose. Further boosting doses may be given to enhance or rejuvenate the response on a periodic basis. 3H 1 can be administered on a weekly, preferably biweekly, basis until a desired, measurable parameter is detected, such as elicitation of an immune response. Administration can then be continued on a less frequent basis, such as bimonthly or monthly, as appropriate. Timing of subsequent injections (i.e., a maintenance dose) will depend, inter alia, upon the condition and response of the individual being treated. Ab3 levels can be monitored, preferably by the diagnostic methods described herein, to determine when maintenance (booster) administrations should be given, which could generally be about every two to three months. In one embodiment, the initial series of administrations is given at biweekly intervals for a total of four injections, followed by monthly injections.

It is understood that for some situations the individual receiving 3H1 may be moderately to severely immunocompromised, either due to the nature of previous treatment, the disease itself, or both. Thus, the time required to mount an immune response and/or the number of injections of 3H1 and/or the amount of 3H1 per administration may vary. For example, an individual may require a longer time to elicit an immune response once 3H1 has been administered. In this case, it is recommended that the individual continue to be monitored for an immune response, even if no initial (i.e., within the first month) immune response has been detected. As another example, an individual may require more than the average number of injections to elicit an immune response. Alternatively, it may be desirable to have the intervals between injections longer than monthly, for example, in order to optimize the immune response, such as a T cell response.

One possible indication of effectiveness of administration of 3H1, or whether administration of 3H1 is indicated, is the density of CEA on the tumor cells. This density can vary widely from individual to individual, and may vary over the course of administration of 3H1 and/or over the course of the disease. As used herein, "density" of CEA can refer to either or both of the following: (a) the number of cells per total cells in a given biological sample that have CEA on their surface; (b) the amount of CEA on the surface of each cell. Density (a) is calculated by noting the number of cells in a sample that are stained or otherwise indicate that CEA is present divided by the total number of cells. This density would be preferably greater than about 20%, more preferably greater than about 30%, more preferably greater than about 50%, even more preferably greater than about 70%, even more preferably greater than about 80%, most preferably greater than about 90%. Thus, the invention includes administration of 3H1 to an individual having density of CEA greater than about 20%, preferably greater than 30%, more preferably greater than 70%, even more preferably greater than about 80%, most preferably greater than about 90%.

Density (b) is indicated by the relative intensity of staining (or intensity of any measurement indicating the presence of CEA) of cells in a sample from one individual relative to, for example, a sample from another individual. For this density, one skilled in the art can make an empirical determination of density. Density (b) is relative to normal tissues (i.e., cells lacking CEA, or unaffected cells), so preferred ranges may be about 1.5 fold, preferably about 3 fold, more preferably about 10 fold higher expression over unaffected cells, as detected by immunohistochemical staining density. Unaffected cells could also be from the same individual.

This is not to say that individuals with lower densities, for example, less than about 50% are not indicated for administration of 3H1. While not wishing to be bound by a single theory, it is possible that administration of 3H1 could elicit a series of immuno-reactions that result in a more general response that is effective against a CEA-associated tumor, such as a cytotoxic T cell response. A lower density, however, may indicate that additional therapies are desirable.

It is understood that density can also be used as an indicator of extent of disease and response to administration of 3H1. For example, a sample taken from an individual at the onset of 3H1 administration may exhibit about 80% density (i.e., about 80% of the cells exhibit CEA). After receiving 3H1, a sample taken from the same location may exhibit only about 50% density, indicating that CEA-expressing cells are being destroyed. Similarly, if the intensity of staining of a sample from an individual receiving 3H1 diminishes upon receiving 3H1, this indicates that CEA-bearing tumor cells are being destroyed.

For the purpose of raising an immune response, 3H1 may be administered in an unmodified form. It may sometimes be preferable to modify 3H1 to improve its immunogenicity. As used herein, "immunogenicity" refers to a capability to elicit a specific antibody or cellular immune response, or both. Methods of improving immunogenicity include, inter alia, crosslinking with agents such as gluteraldehyde or bifunctional couplers, or attachment to a polyvalent platform molecule. Immunogenicity may also be improved by coupling to a protein carrier, particularly one that comprises T cell epitopes.

Administration of 3H1 can occur alone or in conjunction with other forms of therapy, whether established or experimental. "In conjunction with" means 3H1 can be given concurrently with, prior to, or after other therapies. For instance, 3H1 can be used to complement surgery, radiotherapy, chemotherapy and/or other drug therapies, either concomitantly or serially with respect to other therapies. The sequence and timing of these administrations can be determined empirically and will depend on such variables as the disease being treated, the condition of the patient, clinical history and indications, and/or responsiveness to various therapies. Such determinations are within the skill of the art.

Preferably, 3H1 is administered before administration of other, adjunct therapies, such as chemotherapy and/or radiation. Preferably, 3H1 is administered 1 day, preferably 3 to 5 days, before the first course of chemotherapy and/or radiation therapy, and 1 day, preferably 3 to 5 days, prior to each cycle of chemotherapy and/or radiation therapy. This allows the individual more time to mount an immune response.

In one embodiment, 3H1 is administered in conjunction with fluorouracil (Roche Laboratories) and levamisole hydrochloride (Janssen Pharmaceutical; Ergamisol®) or leucovorin calcium (Immunex). These compounds are indicated as adjuvant therapy after surgical resection in patients with Dukes' stage C colon cancer (levamisole), as well as palliative treatment of patients with advanced colorectal cancer (leucovorin). Protocols for administration of these compounds are known in the art and are provided by the manufacturer. Fluorouracil and levamisole are preferably administered as follows: (a) initial therapy, 50 mg levamisole every 8 hours for 3 days starting 7–30 days post surgery; fluorouracil, 450 mg/m$^2$/day intravenously for 5 days starting 21–34 days post surgery concomitant with a 3 day course of levamisole; (b) maintenance therapy, 50 mg levamisole for 3 days every 2 weeks; fluorouracil, 450 mg/m$^2$/day intravenously once a week beginning 28 days after the initiation of the 5 day course. Either of the following regimens can be used for administration of leucovorin: (1) administer leucovorin at 200 mg/m$^2$ by slow intravenous injection over a minimum of 3 minutes followed by fluorouracil at 370 mg/m$^2$ by intravenous injection; (2) administer leucovorin at 20 mg/m$^2$ by intravenous injection followed by fluorouracil at 425 mg/m$^2$ by intravenous injection. Treatment using either regimen is repeated daily for 5 days, which can be repeated at 28 day intervals for two courses, and then repeated at 4 to 5 week intervals. Other regimens can also be used. These doses can be adjusted according to the condition of the individual, such as white blood cell count.

If used with fluorouracil with levamisole or leucovorin, 3H1 is preferably administered before, preferably 1 day before, more preferably 3 to 5 days before, administration of chemotherapy. Administration of 3H1 can continue for various courses, depending on the individual and disease being treated. Preferably, administration of 3H1 is continued for as long as an individual is able to mount an immune response, whether humoral and/or cellular. Administration of 3H1 should be discontinued if the individual displays unacceptable adverse reactions that are associated with the administration of 3H1, and may or may not be continued if the individual displays progressive disease. Continuation of administration of 3H1 in the event of progressive disease depends at least in part on whether continued administration of 3H1 could supplement other indicated therapies.

Determining the Effects of Administration of 3H1

In order to determine the effect of administration with 3H1, an individual may be monitored for either an antibody (humoral) or cellular immune response against CEA, or a combination thereof. The individual can also be monitored for disease progression.

To determine the level of CEA antibody (Ab3) in a biological sample, for example, serum or plasma is obtained from the individual. The sample may optionally be enriched for immunoglobulin before the assay is conducted, although this is not usually required. If a mouse immunoglobulin (such as 3H1) is to be used as an assay reagent, the sample is preferably pretreated to remove anti-mouse immunoglobulin activity. This may be performed, for example, by depletion on a mouse immunoglobulin column, or by mixing non-specific mouse immunoglobulin into the sample and removing any immunoprecipitate formed.

To conduct the assay, anti-CEA that may be in the sample is contacted with a non-limiting amount of an antigenic equivalent of CEA. This may be isolated CEA, nitrocellulose with CEA affixed by direct blotting or by transfer from a polyacrylamide gel, cells expressing CEA (such as LS174-T cells), membrane preparations from such cells, or fixed tissue sections containing CEA. Alternatively, an anti-idiotype, particularly 3H1, may be used.

Once the immune complex has formed, it is generally separated from uncomplexed CEA analog, and the amount of complex present is determined. The complex may be separated, for example, by centrifugation to collect cells or an immunoprecipitate, or capture by a solid phase. The amount of complex present may be measured by providing the CEA analog with a label either directly, or by incubating with a secondary reagent. Alternatively, a competition assay may be performed, in which the sample is first incubated with the CEA analog, and then a non-limiting amount of a labeled anti-CEA reagent is added which competes with the anti-CEA which may be present in the sample. Suitable labels include radiolabels, enzyme labels, fluorescent labels, and chemiluminescent labels. A standard curve is constructed using solutions known to contain no anti-CEA, and solutions with various relative concentrations of anti-CEA, in place of the sample. The sample containing the unknown amount of anti-CEA is generally assayed in parallel, and the relative amount of anti-CEA contained therein is determined by comparison with the standard curve. A preferred assay for determining anti-CEA levels using 3H1 antibody is radioimmunoassay (Example 4).

The isotype of the anti-CEA antibody may be determined by including in the immunoassay an isotype-specific reagent (s), either at the separation or the labeling stage. For example, anti-human IgG may be used to separate or detect antibody of the IgG class present in a clinical sample of human origin. Presence of specific anti-CEA of the IgG class generally indicates a memory response. Presence of anti-CEA of the IgM class generally indicates ongoing immunostimulation, such as may be due to the presence of an CEA expressing tumor, or ongoing treatment with 3H 1.

If desired, anti-CEA antibody detected in a biological sample may be further characterized; for example, by competition with anti-8019 (Ab1) to determine whether they are specific for related epitopes on CEA. Competition assays between Ab1 and Ab3 are described in Example 4.

Anti-CEA antibody may also be tested to determine whether it is cytotoxic. Complement mediated cytotoxicity (CMC) is determined, for example, by using CEA-expressing target cells (such as LS 174T) labeled with $^{51}$Cr. Labeling may be accomplished by incubating about $10^6$ cells with ~200 $\mu$Ci Na$_2$$^{51}$CrO$_4$ for 60 minutes at 37° C., followed by washing. The assay is conducted by incubating the antibody (or clinical sample containing the antibody) with the target cells. The opsonized cells are then washed and incubated with a source of complement; for example, guinea pig serum pre-adsorbed to remove intrinsic antibody activity. After a suitable incubation period at 37° C., release of $^{51}$Cr into the medium is determined and compared with that from unopsonized control cells. Release of $^{51}$Cr correlates with CMC activity.

Another way of characterizing the anti-CEA antibody is by testing its ability to participate in an ADCC response (Cheresh et al. (1986) *Cancer Res.* 46:5112). Radiolabeled CEA-expressing target cells are incubated with the anti-CEA (in the form of heat-inactivated serum), and effector cells. Normal human peripheral blood mononuclear cells (PBMC) are suitable effector cells, and preferably are used at an effector:target ratio of about 100. After approximately 4 hours at 37° C., the proportion of released $^{51}$Cr is determined as a measure of ADCC activity. ADCC activity in high-risk patients' sera is shown in Example 4.

The cellular immune response in a subject being administered 3H1 may be quantified by conducting standard functional assays for specific T cell activity.

One type of assay measures T cell proliferation. In this test, peripheral blood mononuclear cells (PBMC) are obtained from a whole blood sample collected from the treated individual. For experimental animals, spleen cells may also be used. T cells may be enriched, for example, by centrifugation on a gradient such as FICOLL™. The cells are then cultured in the presence of CEA or (more usually) irradiated CEA expressing cells at various concentrations. Preferably, the stimulator cells are autologous with the responder cells, particularly in terms of histocompatibility Class II antigens. Extent of proliferation is then measured (often in terms of $^3$H-thymidine incorporation) in comparison to unstimulated cells. T cell proliferative activity in high risk patients' sera is shown in Example 4.

Another type of assay measures T cell cytotoxicity. In this test, an enriched T-cell population is used to effect lysis of $^{51}$Cr-labeled CEA expression target cells, prepared as described above. Preferably, the effector cells are autologous with the target cells, particularly in terms of histocompatibility Class I antigens. The T cell population may optionally be pre-stimulated with CEA or a relevant cell line. The T cells are then combined at various ratios with about $10^4$ labeled target cells; for example, in wells of a microtiter plate. The plate is optionally centrifuged to initiate cell contact, and the cells are cultured together for 4–16 hours at 37° C. The percent specific release of $^{51}$Cr into the medium is measured in comparison with labeled targets cultured alone (negative control) and targets lysed with a detergent such as 0.1% Triton™ X-100 (positive control).

Other relevant measurements to determine the effect of 3H1 administration include clinical tests as may be appropriate in determining the development (i.e., progression) of cancer of the suspected type, whether direct or indirect indications of disease progression. Such tests may include blood tests, mammography, radioscintigraphy, CT scan, and MRI. Any measurable variable that correlates with disease progression is suitable. For instance, for CEA-associated tumors or disorders that are associated with measurable CEA in blood, CEA levels can be measured. Methods for measuring serum levels of CEA are known in the art and are commercially available as diagnostic kits (Hybritech Enzyme Immunoassay). For this test, serum is prepared as follows: Individuals treated with 3H1 will have 0.5 ml of serum treated with 1 ml of acetate buffer (pH 5.0) followed by heating at 90° C. for 15 minutes. After centrifugation at 2000 rpm for 10 minutes, the clear supernatant is tested for CEA as described in Example 4. The serum should be heat inactivated prior to testing as described because commercial CEA kits include a murine anti-CEA antibody and individuals receiving 3H1 usually have human mouse antibody (HAMA). Any other tumor-associated marker is suitable for monitoring the course of therapy, such as, for example, CA-125.

The invention also includes use of 3H1 for preparation of a medicament for use in treatment of CEA-associated tumors, especially in those individuals with low tumor burden.

The following Examples are provided to illustrate but not limit the invention.

EXAMPLE 1

Production of 3H1 Anti-Idiotype Antibody for Immunization

Murine monoclonal antibody 8019 (recognizing a distinct epitope of CEA) was used to immunize syngeneic BALB/c mice for the production of anti-idiotype antibody 3H1 (IgG1-κ) as described in commonly owned patent application Ser. No. 08/579,940. See also Bhattacharya-Chatterjee et al. (1987) *J. Immunol.* 139(4):1354–1360; Bhattacharya-Chatterjee et al. (1988) *J. Immunol.* 141:1398–1403. Immunization of BALB/c mice, hybridoma fusion and cloning, selection of anti-idiotype (Ab2) and production of ascites in bulk quantities in mice were done as previously described. The Ab2 anti-idiotype 3H1 (IgG1) was purified from ascites by affinity chromatography on protein A-CL Sepharose 4B column followed by DEAE-Sepharose ion-exchange chromatography. The purity of the isolated immunoglobulin (>95%) was determined by sodium dodecylsulfate polyacrylamide gel electrophoresis (SDS-PAGE) and high pressure liquid chromatography techniques. Sterility, pyrogenicity, polynucleotides, mycoplasma and adventitious virus contamination and retrovirus removal validation tests were done in accordance with the United States Food and Drug Administration guidelines.

To 5 mg aliquots of purified mAb anti-Id (3H1), 1 ml of 2% Alu-Gel S (Serva Fine Biochem, Inc., Garden City, Long Island, N.Y.) was added. The volume was then adjusted to 10.0 ml with D-PBS and the mixture incubated on a vortex for one hour at room temperature. The mixture was then centrifuged at 2000 rpm at 24° C. for 10 minutes. The amount of mAb bound in the gel layer was determined by measuring spectrophotometrically the amount of unbound antibody in the supernatant. The Alu-Gel precipitated antibody was stored at 4° C. until use. These procedures were performed aseptically in a laminar flow hood and the final product was sterile and clearly labeled as anti-Id 3H1 Alu-Gel and aliquoted into pyrogen-free, sterile glass vials.

EXAMPLE 2

Amelioration of Tumor Burden in Mice by Administration of 3H1

We used a CEA tumor model in syngeneic C57BL/6 (H-$2^b$) mice to evaluate tumor specific immunity induced by 3H1. Robbins et al. ((1991) *Cancer Res.* 51:3657–3662) have reported the development of a transduced mouse tumor line which expresses CEA at high concentrations. This cell line, MC-38cea, appears to be an excellent target for cell mediated and humoral immunity. Nontransduced MC-38 as well as the CEA transduced cell lines were kindly provided by Dr. Jeffrey Schlom of NCI.

Mice were immunized with 3H1-KLH conjugate (50 μg/mouse). The first immunization of mice was done intra-peritoneally using Freund's complete adjuvant. Subsequent weekly immunizations were subcutaneous with Freund's incomplete adjuvant. Serum was drawn from tail veins of mice one week after each immunization and tested for Ab3 response by RIA on Ab2 (3H1) coated plate and anti-CEA (Ab1') response by ELISA on purified CEA coated plate. Spleens from 3 mice were pooled for assay of T cell proliferation. For ADCC, target MC-38-cea cells were labeled with [$^{51}$Cr]sodium chromate and incubated with spleen cells from immunized mice. Percent release was the proportion of experimental to total released radioactivity corrected for spontaneous (baseline) release. Total release was determined by measuring radioactivity upon addition of 1% Triton X-100 to the labeled cells. Spontaneous release was determined by assays of radioactivity released from $^{51}$Cr-labeled cells. MC-38 and MC-38-cea cells were grown in DMEM containing 10% FCS, 1%-L-glutamine, 100 μg/ml penicillin, and 0.25 μg/ml streptomycin. MC-38-cea cells were cultured in the presence of 200 μg/ml neomycin analog G-418.

Figure 1B:
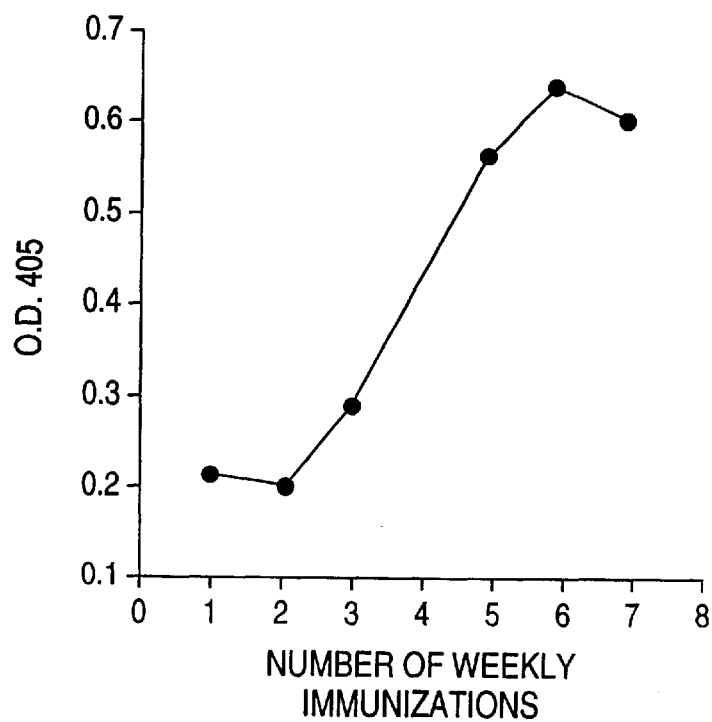
Figure 1C:
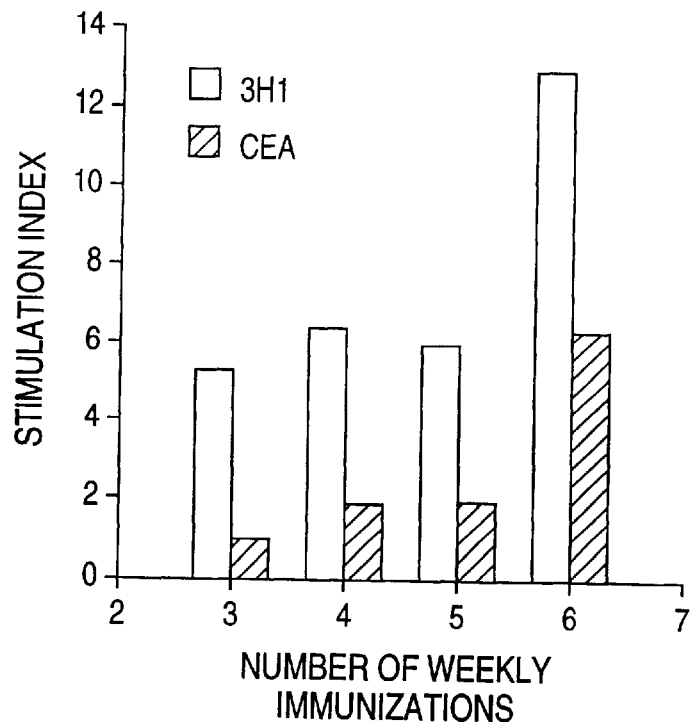
Figure 1D:
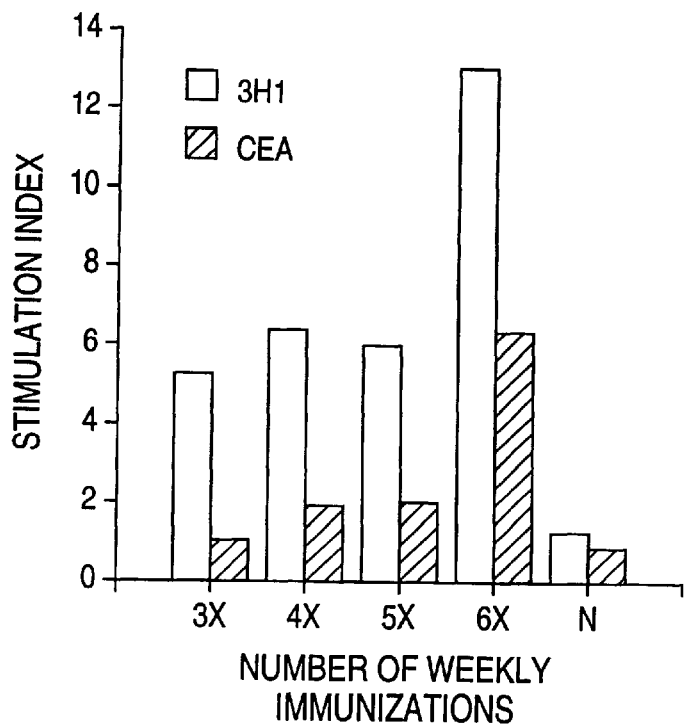
Figure 8A:
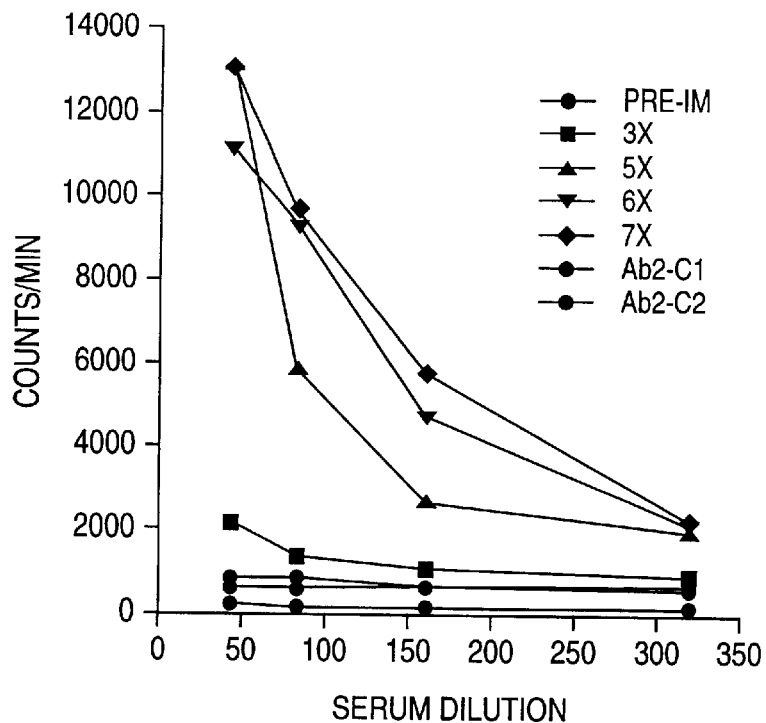
FIGS. 8(A) and (B) are graphs depicting detection of an immune response to 3H1 in mice at varying dilutions of sera.
Figure 8B:
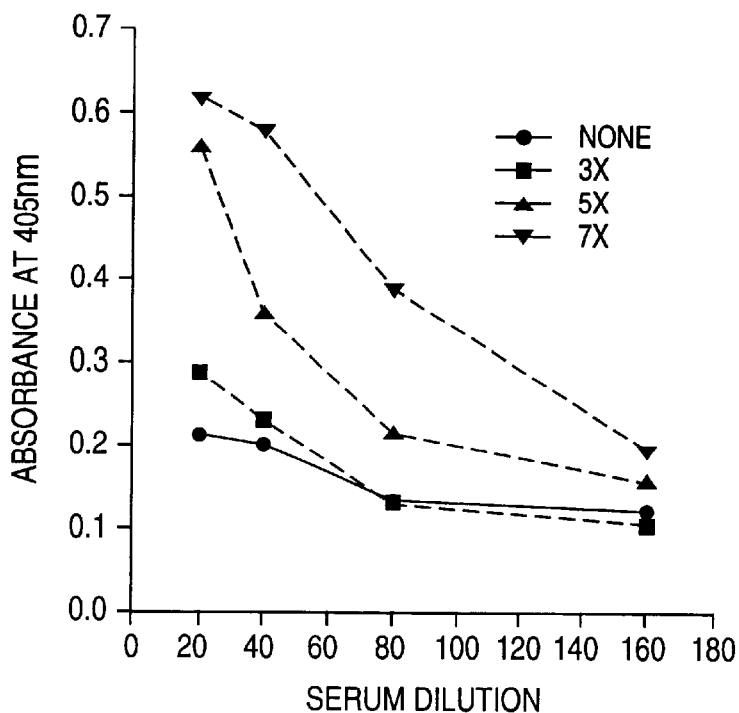
FIG. 8(B) depicts an assay of anti-CEA (Ab1') antibody.

Results described in FIG. 1 show that 5 immunizations were necessary for the induction of a significant amount of Ab3 (FIG. 1A) and Ab1' (FIG. 1B). Data in FIG. 8(A) show that Ab3 was detectable in sera of immunized mice even after a 300-fold dilution. The data in FIG. 8(B) show that Ab1' could be detected in sera of immunized mice even after an 80–160-fold dilution. Idiotype and CEA-specific T cell proliferation also peaked after 5–6 immunizations (FIG. 1C).

The idiotype of Ab3 induced in mice by 3H1 vaccine was analyzed by inhibition of binding Ab1 and Ab2 by mouse serum. Results of these experiments are shown in Table 1. For these experiments, serum from each of 5 mice was separately assayed to obtain the mean and S.E. In the Ab1–Ab2 binding inhibition assays, inhibition by control normal serum pool varied between 10 and 15%, and inhibition was complete with 2.5 μg of 8019. In the cell binding inhibition assay, inhibition by normal serum was at the background level.

TABLE 1

Idotype analysis of Ab3 induced in mice immunized with 3H1-KLH conjugate

| Serum dilution | Ab1–Ab2 Inhibition | | Inhibition of binding to CEA-positive cells |
|---|---|---|---|
| | 8019 coat/ 3H1 binding | 3H1 coat/ 8019 binding | |
| 20 | 87 ± 4 | 89 ± 3 | 53 ± 7 |
| 40 | 78 ± 8 | 85 ± 4 | 25 ± 6 |
| 80 | 64 ± 9 | 72 ± 7 | 14 ± 4 |

Binding of Ab1 (8019) to 3H1 was inhibited by serum from 5 of 5 immunized mice, regardless of which antibody was used to coat the plates. Inhibition of binding of $^{125}$I-labeled 8019 to CEA was determined by using CEA-positive MC-38-cea cells. Again, sera from 5 of 5 mice inhibited this binding, and the inhibition was significant, even after 8-fold dilution of the serum. These results suggested that the Ab3 induced in mice by the 3H1-KLH conjugate share the same idiotype as Ab1.

Figure 9A:
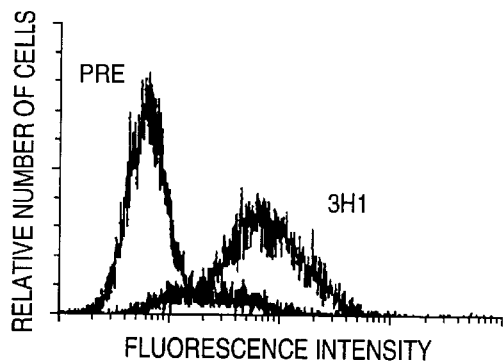
FIGS. 9(A)–(F) are tracings of flow cytometric analysis of Ab1' generated in mice by immunization with 3H1.
Figure 9D:
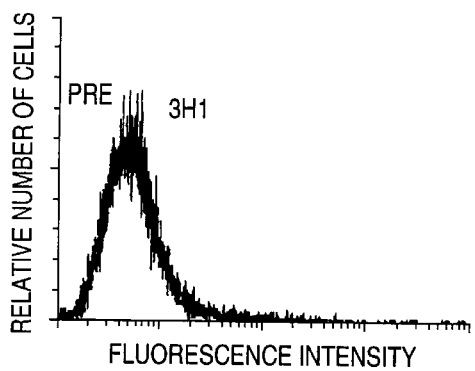
Figure 9B:
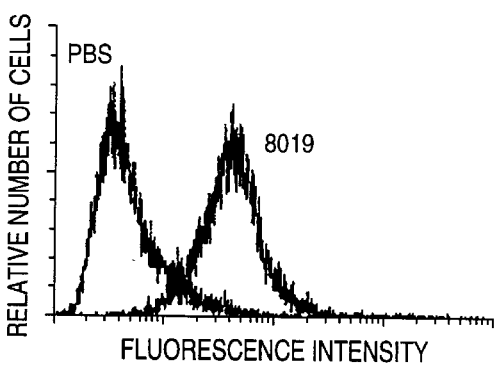
Figure 9E:
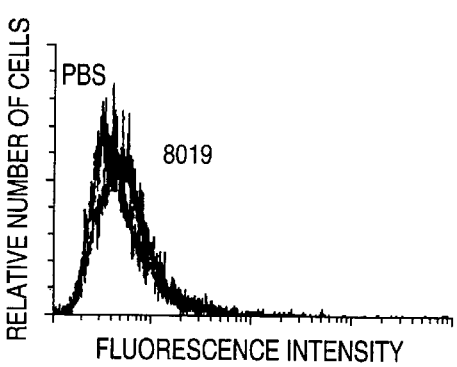
Figure 9C:
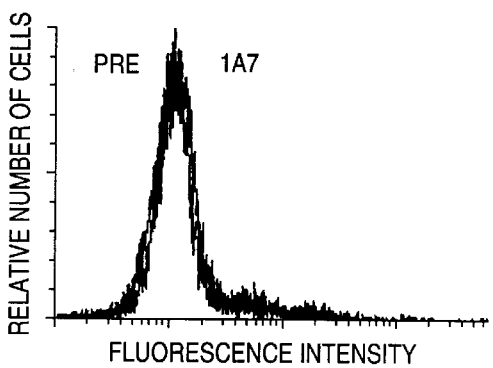
Figure 9F:
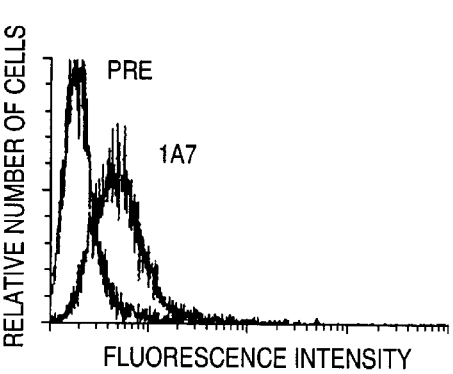

To further verify the nature of Ab1' induced by 3H1 vaccination, flow cytometric analysis of pre-immune sera and pooled sera from three mice after six immunizations with the 3H1-KLH conjugate was performed. Results presented in FIG. 9 demonstrate that sera from mice immunized with the 3H1 vaccine can bind to the MC-38-cea cell surface (FIG. 9A) identical to the monoclonal anti-CEA antibody, 8019 (FIG. 9B), whereas no binding was observed with preimmune sera or sera of mice immunized with isotype-matched anti-idiotype antibody, 1A7 (FIG. 9C). CEA-negative MC38 cells did not bind sera from mice immunized with 3H1 vaccine (FIG. 9D), monoclonal anti-CEA antibody 8019 (FIG. 9E), or with sera of mice immunized with 1A7 (FIG. 9F).

Figure 10:
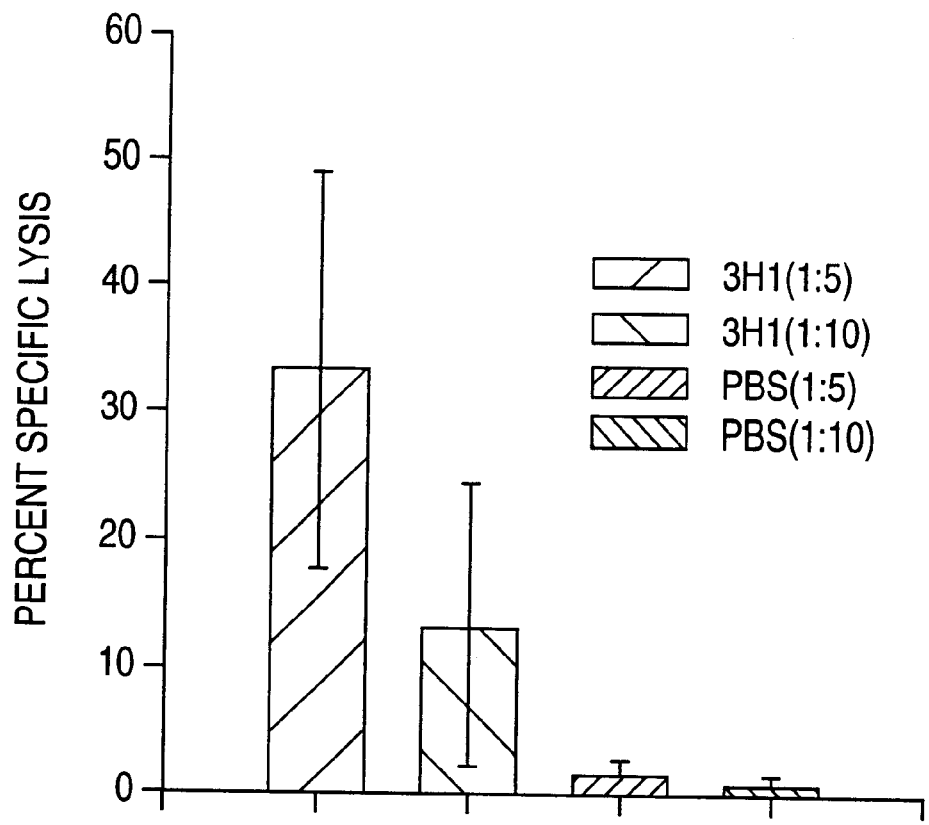
FIG. 10 is a bar graph depicting ADCC by serum from mice immunized with 3H1. Diagonally hatched bar denotes 3H1 (1:5); open bar denotes 3H1 (1:10); cross hatched bar denotes PBS (1:5); vertically hatched bar denotes PBS (1:10).

To determine whether the Ab1' generated 3H1 immunization is cytolytic for CEA-positive tumor cells, such as MC-38-cea, ADCC was determined. Results of the ADCC experiments are summarized in FIG. 10. Although the extent of specific cell lysis by sera from each individual mouse varied (33±7, 1:5 dilution; 13.2±5, 1:10 dilution), significant ADCC was observed in 5 of 5 mice. Negligible ADCC was observed with sera from mice immunized with PBS (FIG. 10).

To evaluate the effect of this vaccine for therapy of established tumors, a batch of mice was injected with $5 \times 10^5$ MC38cea cells. After 3 days, one group of mice was treated with 3H1 vaccine at 4 day intervals. The control group was treated with another anti-Id, 11D10, which recognizes a breast tumor associated antigen. The results are shown in Table 2. Tumors grew in both groups, but tumors of 6 of 9 mice treated with 3H1 vaccine became necrotic after 5–6 courses of therapy and regressed. The differences between the two groups were significant at P <0.05 by Fisher's exact test. Only 1 of 8 mice had tumor necrosis in the group treated with the control anti-Id vaccine, 11D10. From these results we concluded that 3H1 has tumor specific therapeutic effect.

TABLE 2

Therapy of Established Tumor of Mice with 3H1 and Control AB2

| Vaccine | No. with regression | No. with growing tumor |
|---|---|---|
| 3H1-KLH | 6 | 3 |
| 11D10-KLH | 1 | 7 |

EXAMPLE 3

Delay of Tumor Development in Mice Receiving 3H1

Figure 2A:
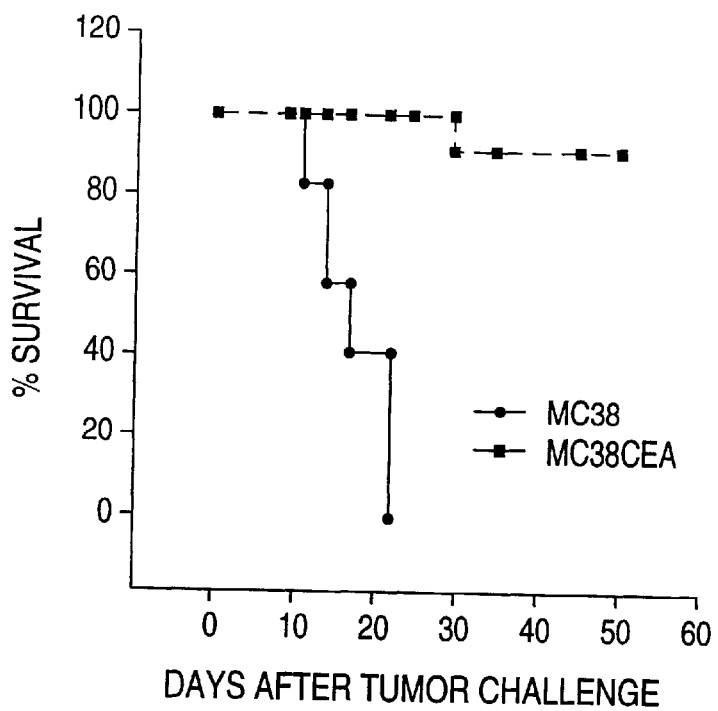
FIG. 2(A) shows percent survival of mice immunized with 3H1-KLH.
Figure 2B:
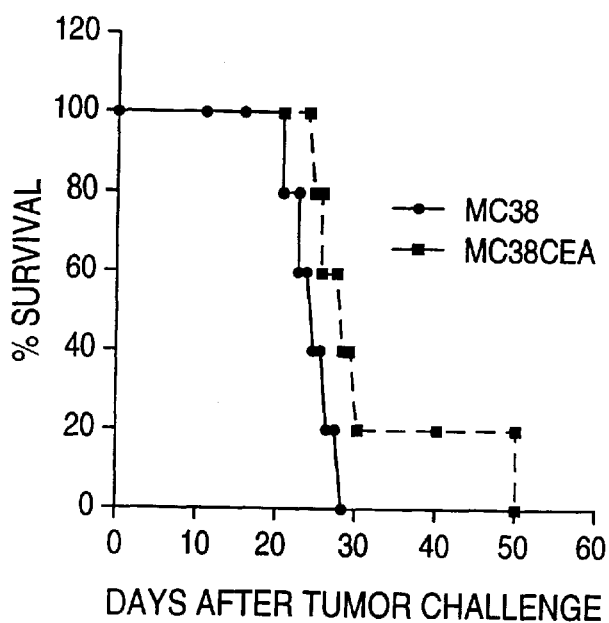
FIG. 2(B) shows percent survival of mice immunized with isotype matched anti-idiotype antibody 11D10 conjugated to KLH.
Figure 2C:
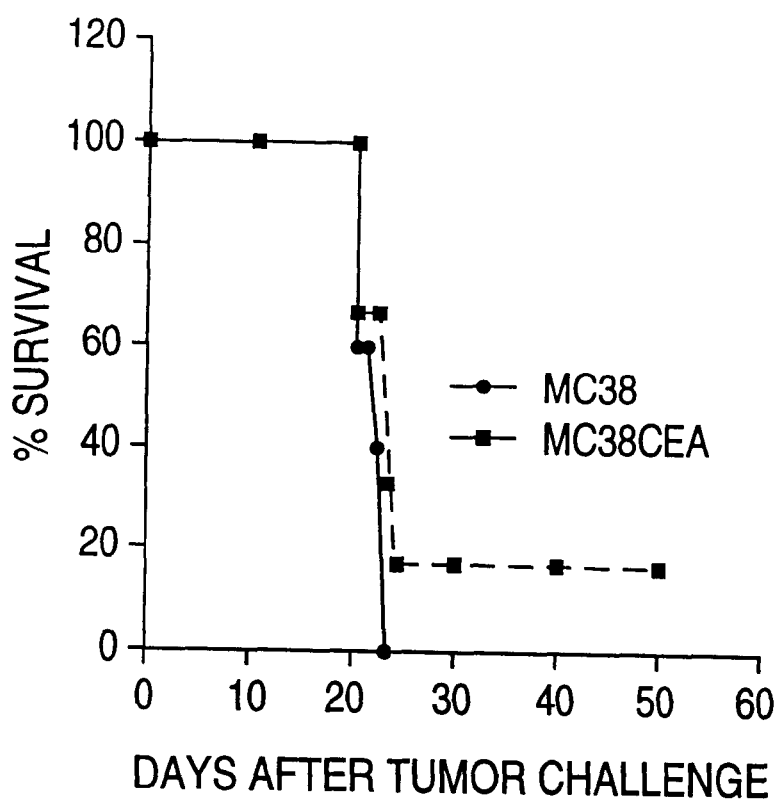
FIG. 2(C) shows percent survival of mice immunized with PBS.

C57BL/6 ($H-2^b$) mice were immunized as described in Example 2. A tumor challenge experiment was started 2 weeks after the sixth immunization. A batch of C57BL/6 mice immunized as described above were divided into 2 groups of 12 mice each. The first group was challenged with $5 \times 10^5$ MC38cea tumor cells and the second group was challenged with an equal number of MC38 tumor cells. There was a delay of tumor development in mice challenged with MC38cea. The results are shown in FIG. 2. Tumors developed in these mice soon became necrotic and the survival of the mice were prolonged considerably. 3H1-immunized mice injected with CEA negative colorectal tumor cells, MC38, developed palpable tumor within 7–10 days and died within 2–3 weeks. Other control groups (mice immunized with an unrelated anti-Id (11D10; FIG. 2B) and those vaccinated with PBS (FIG. 2C)) when challenged with MC38cea cells also died within 2–3 weeks.

These experiments show prolonged survival of mice (i.e., delay in tumor development) receiving 3H1 when challenged with CEA tumor cells.

EXAMPLE 4

Use of 3H1 to Treat High Risk Individuals in the Adjuvant Setting

Selection of Patients

Six high risk patients with CEA-positive tumors were selected for this study (Table 3). Three of the patients (#1, #2, #3) had had surgery for Duke's C carcinoma and were receiving 5-FU and levamisole. Two of the patients had high-risk adenocarcinomas of the lung (#4, Stage IV, surgically resected; #5, Stage II, resected, two positive peribronchial lymph nodes). One patient (#6) had surgical resection of a second recurrence of colorectal cancer. Baseline studies included complete physical examination, chest radiography, computer axial tomography examination of the abdomen, serum CEA level, routine blood counts and chemistries. All of the patients had been off prior therapy for at least four weeks and staging was repeated at the conclusion of therapy.

TABLE 3

Patient Characteristics

| Patient No. | Age/Sex | Dosage (mg) | Origin Disease | Baseline CEA Level | Humoral Response | Cellular | On Study | Current Status |
|---|---|---|---|---|---|---|---|---|
| 1 | 66/M | 2 | colon | <3.0 ng/ml | + | + | 7/94 | progression after 21 mos. |
| 2 | 66/M | 2 | colon | <1.0 ng/ml | + | + | 9/94 | no detectable disease |
| 3 | 20/F | 2 | colon | <3.0 ng/ml | + | + | 3/95 | no detectable disease |
| 4 | 38/M | 2 | colorectal | <1.0 ng/ml | + | + | 5/94 | progression after 20 mos. |
| 5 | 68/F | 2 | lung | 4.5 ng/ml | + | + | 4/95 | no detectable disease |
| 6 | 48/M | 2 | lung | <1.0 ng/ml | + | + | 3/94 | no detectable disease |

Preparation of Ab2

3H1 was obtained and alum-precipitated as described in Example 1. The final product was tested for sterility, pyrogenicity and general safety in guinea pigs before use. An Investigational New Drug Application was approved through the United States Food and Drug Administration (BB-IND 5055). Before administration, 3H1 was heat treated in the presence of adjuvant at 45° C. for 30 minutes in a water bath.

Treatment Schedule

All six patients received 2 mg of heat-treated, alum-precipitated 3H1 intracutaneously. Four injections were given every two weeks, followed by monthly injections. Patients were evaluated every 12 weeks. For patients receiving fluorouracil (5-FU) and levamisole concurrently with 3H1 (patients #1,2 and 3), 3H1 was administered 2–5 days prior to administration of 5-FU. Patients were removed from this study if they demonstrated progressive disease.

Toxicity and Clinical Responses

Toxicity was minimal with only local reactions at the injection site with mild erythema and induration and mild fever and chills relieved by acetaminophen. The anti-idiotypic treatment did not have any deleterious effect on hematopoietic cells, renal or hepatic function. Patients were monitored very closely for disease activity.

Purified CEA

Purified CEA was obtained commercially from Rougier Bio-tech, Montreal, Canada (cat. no. 70015). CEA was isolated from human liver metastasis of colonic tumors by perchloric acid extraction and purified twice by ion-exchange chromatography followed by gel filtration and several steps of HPLC chromatography. The CEA is 100% pure, produced a single band at 180,000 m.w. by high power liquid chromatography and SDS-PAGE and was immuno-precipitated as a single band by horse as well as rabbit anti-CEA antibody. The CEA preparation was resolved into two closely migrating bands at 180,000 and 200,000 m.w. by Western blot analysis using murine monoclonal antibody anti-CEA. We rechecked the material by Western blot analysis using monoclonal antibody 8019.

Serial Monitoring of Circulating CEA

Indirect measurement of extent of disease (CEA level) was recorded prior to immunization and determined after each immunization and then once monthly following completion of the immunization schedule. For this, patients' sera were heat-inactivated to precipitate the immunoglobulins which would interfere with the CEA monitoring assays involving murine monoclonal Ab1. CEA is heat stable, and was measured in the clear centrifuged supernatant by routine ELISA assay (Hybritech Enzyme immunoassay kit, cat. no. 4063). The serial monitoring of CEA correlated with disease progression and all patients who clinically progressed and a rise in their serum CEA levels except patients who did not secrete CEA.

CEA was quantified in heat-extracted serum. For this, 1 ml of 0.2 M sodium acetate buffer, pH 5.0 was added to 0.5 ml of serum, vortex-mixed, incubated for 15 min. at 900 C., and centrifuged (1200×g, 10 min). The supernatants were assayed the same day or stored frozen at −20° C. until assay. One hundred microliters of supernatant was then assayed by the enzyme immunoassay for CEA as described (Hansen et al. (1989) *Clin. Chem.* 35(1):146–151).

Assays for Humoral Immunity (a) Total anti-3H1 Response

The development of humoral immunity induced by immunization with alum-precipitated 3H1 was assessed by testing sera obtained from patients before therapy and after each treatment with the vaccine. The sera were initially tested for total human anti-murine-antibody responses including anti-iso/allo/and anti-anti-idiotype antibodies by sandwich radioimmunoassay as described by Khazaeli et al. (1988) *J. Nat'l Cancer Inst.* 80:937–942. Briefly, microtiter plates were coated with 3H1 and incubated with different dilutions of patients' sera. After washings, the antigen-antibody reaction was tagged using $^{125}$I-labeled anti-Id 3H1 in a homogeneous sandwich radioimmunoassay. Since 3H1 is injected as intact IgG1, patients are expected to mount human anti-mouse antibody responses.

Hyperimmune sera (following the fourth injection of 3H1) from all six patients showed significant levels of total human anti-mouse antibody responses including anti-iso/allo/and anti-anti-idiotypic antibodies against immunizing Ab2, 3H1, as determined by homogeneous sandwich radioimmunoassay.

(b) Specific Ab3 Response to Ab2

Sera from these immunized patients were checked for their ability to inhibit the binding of $^{125}$I-labeled Ab1 (8019) to Ab2 (3H1) on the plate by radioimmunoassay or vice versa (inhibition of radiolabeled Ab2 binding to Ab1 on the plate). These reactions were done in the presence of excess normal murine immunoglobulin to block human antibodies against isotypic and allotypic determinants.

Crude sera obtained from patients after the fourth treatment were pre-incubated with normal murine immunoglobulin to block human antibodies against isotypic and allotypic determinants. We routinely used post fourth immunization because a minimum of four immunizations were necessary in animal models to induce immunity. For patients who received more than four injections, immune responses remained comparable or continued to increase in titer. Serial dilutions of sera were then tested for inhibition in the Ab1–Ab2 binding assay. All assays were performed in triplicate. For direct binding inhibition assay between Ab1 and Ab2, purified 3H1 (Ab2) was used to coat plates (500 ng/well) and the binding of radiolabeled 8019 (Ab1) to Ab2 was tested for inhibition in the presence of different patients' hyperimmune Ab3 sera and Ab1. This demonstrated whether Ab3 in patients' sera shared idiotopes with 8019 (Ab1). Also, this inhibition assay between Ab1–Ab2 binding by Ab3 sera indicated whether Ab3 is a true anti-anti-idiotype. Unrelated Ab3 was used as control. After washings, the antigen-antibody reaction was tagged using $^{125}$I-labeled anti-idiotype reagent in a homogeneous sandwich radioimmunoassay as above. Pretreatment, nonimmune sera and sera from normal donors were used as controls.

Figure 3:
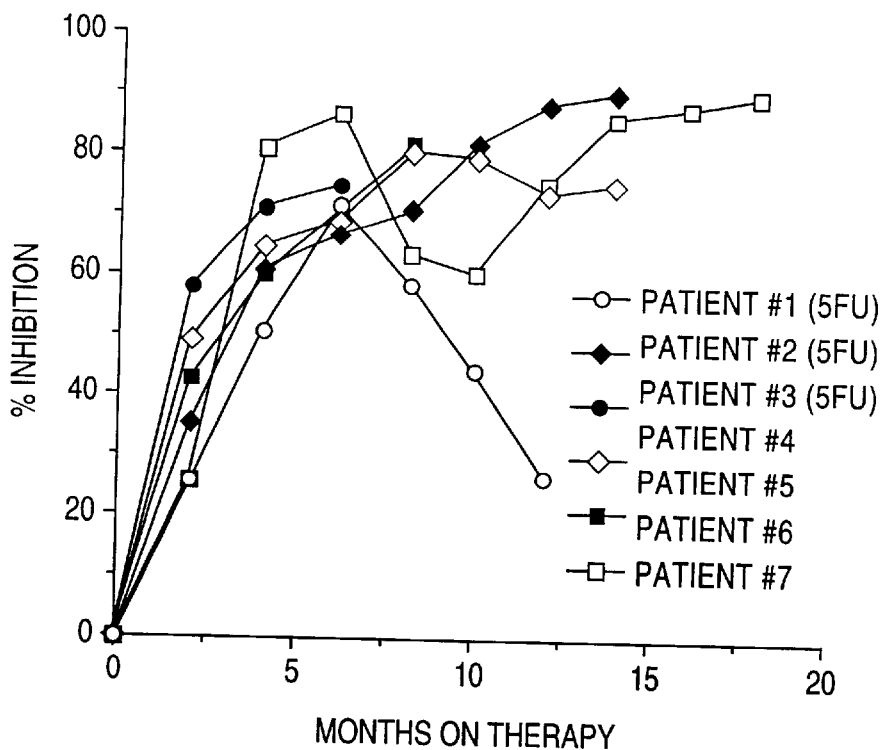
FIG. 3 is a graph depicting inhibition of binding of Ab1 (8019) to Ab2 (3H1) the presence of 6 high risk patients' sera (after administration of 3H1). Squares with dots in the center denote patient #1; solid diamonds denote patient #2; solid squares with open center denote patient #3; open diamonds denote patient #4; solid squares denote patient #5; open squares denote patient #6. Patients #1–3 were receiving fluorouracil (5-FU) and levamisole concurrently with 3H1.

FIG. 3 shows data from all 6 patients. All six patients generated Ab3. FIG. 3 shows inhibition of Ab1 binding to Ab2 by patients' sera for as long as 20 months into therapy. Only one patient (#1) showed significant decrease, although even this patient showed marked inhibition for 5 months of therapy. This patient eventually displayed disease progression and was removed from the study. Although steric hindrance by Ab3 binding can not be excluded in these assays, the results suggest the presence of true anti-anti-idiotypic antibodies that share idiotypes with Ab1. All 6 patients were positive for Ab3 responses by this assay.

(c) Induction of Anti-CEA Antibodies by 3H1

This assay was conducted to determine whether some of the Ab3 induced in patients by monoclonal murine Ab2 were of the Ab1 type and will bind to CEA. A pure preparation of CEA obtained from Rougier Biotech (as described above) was used to reduce the risk of obtaining false positive results due to nonspecific binding. Purified CEA was radioiodinated with $I^{125}$ by the Chloramine T method. Radiolabeled CEA ($1\times10^6$ cpm) was reacted with 0.5 ml of patient's serum pre-adsorbed on protein G-Sepharose beads. After reactions, the beads were washed and counted in a gamma-ray spectrophotometer. Each sample was performed in duplicate and the mean of the cpm bound is shown. Pre-immune sera, phosphate buffered saline-bovine serum albumin as well as Ab3 sera obtained from a patient treated with an unrelated murine monoclonal antibody for T cell lymphoma were used as controls in these assays.

Immunization with 3H1 induced antibodies that bound to radiolabeled CEA in all 6 patients as determined by radioimmunoassay or ELISA. Pre-treatment, non-immune sera and sera from normal donors were used as controls in these assays.

(d) Competition of Ab1 and Patients' Ab3 for Binding to LS 174-T Cells

If Ab3 has a similar binding site as Ab1, it should compete with Ab1 for binding to CEA on LS 174-T cells. A fixed amount of radiolabeled 8019 (~90,000 cpm) was co-incubated with different concentrations of patient's purified Ab3 or Ab1 preparations and LS174-T cells.

Ab3 was purified from patients' sera as follows. Fifty milliliters of hyperimmune serum were passed over an immunoadsorbent column consisting of immunizing anti-idiotype immunoglobulin (3H1) coupled to Sepharose 4B. Anti-anti-idiotypic antibodies (Ab3) bound to the column were eluted with 0.1 M glycine-hydrochloric acid buffer (pH 2.4). The eluted antibody was neutralized with 3M tris, dialyzed against PBS, pH 7.2 and then passed over an immunoadsorbent column consisting of allotype matched normal mouse immunoglobulin coupled to Sepharose 4B to remove anti-isotypic and anti-allotypic reactivities. Antibody that passed through was concentrated and used as purified Ab3. The isotype of Ab3 was determined by ELISA using human anti-isotype specific reagents (Tago).

Overall, the inhibition curves obtained with Ab1 and Ab3 were very similar at different dilutions. This indicated that the patients' Ab3 bound to the same antigenic epitope as Ab1 and therefore contained antibody molecules with Ab1 properties.

(e) Immunoprecipitation of CEA by Ab1 and Ab3

Purified CEA was labeled with $^{125}$I by The Chloramine T-method and reacted with purified Ab3 (10 µg) or Ab1 (10 µg) or unrelated control Ab3 from lymphoma patient (10 µg) or PBS-BSA control, previously adsorbed on to protein G-Sepharose beads. After washings, The antigen-antibody coated beads were analyzed by SDS-PAGE according to the method of Laemmli ((1970) *Nature* 227:680–685) and radioautographed.

It had been previously shown that Ab1 8019 specifically immunoprecipitated the 180,000 m.w. CEA by SDS-PAGE analysis (Bhattacharya-Chatterjee (1990)). To confirm that the Ab3 induced by 3H1 was specific for the CEA molecule, the iodinated purified CEA preparation was immunoprecipitated by purified Ab3 preparations obtained from two patients as well as Ab1 and analyzed by SDS-PAGE. The results indicate that patients' Ab3 precipitated the same 180,000 m.w. CEA band as that of murine Ab1 8019. There was no cross-reactivity when the iodinated CEA was reacted with purified Ab3 obtained from a patient treated with an unrelated Ab2 (4DC6).

(f) Antibody-dependent Cellular Cytotoxicity

Figure 4:
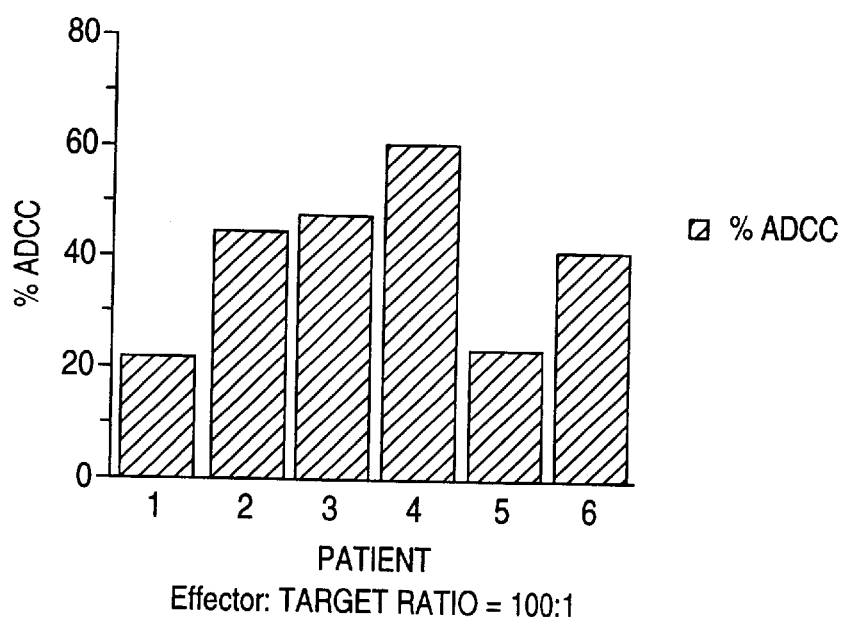
FIG. 4 is a bar graph depicting antibody dependent cellular cytotoxicity (ADCC) in the sera of 6 high risk patients receiving 3H1. The first through sixth bars represent patient numbers 1 through 6, respectively.

We then tested patients' sera for ability to mediate antibody dependent cellular cytotoxicity (ADCC). Cheresh et al. (1986) *Cancer Research* 46:5112–5118. For this assay, cultured human LS-174T cells (which express CEA on the cell surface) were used as target cells and were labelled with $^{51}$Cr. Normal human peripheral blood mononuclear cells (PBMC) were used as effector cells. The ADCC assay was performed in the presence of heat inactivated patient's serum with an effector to target cell ratio or 100:1 for 4 hours, followed by measurement of amount of $^{51}$Cr released. The results are shown in FIGS. 4 and 5. We found that the polyclonal human anti-anti-idiotype antibody response to 3H1 mediates ADCC.

Assay for T Cell Proliferative Response

Cellular immune responses were measured by the proliferation of peripheral blood mononuclear cells incubated with aluminum hydroxide precipitated anti-idiotype antibody 3H1 and aluminum hydroxide precipitated isotope matched control anti-idiotype antibody 4DC6.

Peripheral blood mononuclear cells were isolated from blood obtained after four immunizations by standard Ficoll-Hypaque density gradient centrifugation method and $5\times10^6$ cells per well were incubated with different concentrations of 3H1-Alugel and control 4DC6-Alugel (10 µg to 2 µg) in RPMI medium with 5 percent heat-inactivated fetal calf serum and penicillin and streptomycin. The non-specific mitogen phytohemagglutinin-P was used as a positive control at 2 µg and 1 µg per well. After the cells were incubated for five days at 37° C. in an atmosphere containing 5 percent carbon dioxide, they were pulsed with $^3$H-thymidine (1 µCi per well) for 20 hours. $^3$H-thymidine incorporation was measured in pre and post-therapy samples. Data were expressed as mean counts (triplicate wells) per minute of $^3$H-thymidine incorporation. The Standard Deviation of the data was <10% for each determination.

Peripheral blood mononuclear cells isolated from some selected patients were also incubated with different concentrations of purified CEA (10 ng to 250 ng) and peptides based on sequence homology between 3H1 (IYRANRLIDGV; SEQ ID NO:1) and CEA (PPAQYSWLIDGN; SEQ ID NO:2) as per protocol above.

Positive proliferative responses were seen in all six patients. Pre-immune cells had no proliferative response to the anti-idiotype antibody while hyperimmune cells had a significant response. There was also a response to the isotope matched 4DC6 aluminum hydroxide-precipitated anti-idiotype antibody; this response was significantly less than that of the 3H1 response, likely representing a response to the non-idiotype components of the immunoglobulin molecule. The difference in the response to 3H1-Alugel compared to control 4DC6-Alugel was significant ($p<0.003$) as was the response to CEA compared to BSA ($p<0.005$). There was no response to Alugel itself. Three of the six patients showed proliferative response to the peptides.

Survival Results

Four of these six patients remained disease-free 1–2.5 years following the initiation of 3H1 therapy, with one of the five disease free after 2.5 years. One patient (patient #3) showed progression after 21 months. Another patient (#6; discussed below) showed progression after 20 months.

EXAMPLE 5

Long Term Survival of an Extremely High Risk Patient with CEA-Associated Tumors using 3H1

One patient from the study in Example 4 (#4) had a previous history of colorectal cancer, with two separate pelvic recurrences which had been surgically resected over a course of two years. This patient had an enormously high risk of recurrence, with a greater than 90% risk of recurrence within 12 months after the last resection. The patient was placed on a regimen of 3H1 as described in Example 5.

This patient demonstrated an excellent humoral and cellular response, and remained disease-free (i.e., no detectable disease) for 21 months after treatment began. After twenty-one months of treatment, a CAT scan revealed retroperitoneal lymph nodes and possible metastatic disease of the liver.

EXAMPLE 6

Additional Data Regarding use of 3H1 to Treat High Risk Individuals in the Adjuvant Setting The study described in Example 4 has been extended to contain a total of 15 patients. The protocol and tests were as described in Example 4. Table 4 provides the data regarding all of the patients (numbering corresponds to Table 2). All additional patients had previously received therapy (i.e., surgical resection, radiotherapy, and/or chemotherapy).

of time to progression (from the date of entering the study) was one month to 36 months, with 6 of these patients not progressing until after 20 or more months of treatment with 3H1. Of the 8 patients who have not progressed, one patient (#8) is still disease-free after 11 months of treatment. It is estimated that a patient with the same medical history as Patient #5 (who progressed after 23 months) would have approximately an 80% probability of recurrence within 12 months. As described in Example 5, it is estimated that, based on medical history, Patient #4 (who progressed after 21 months) had over a 90% chance of recurrence within 12 months.

Another useful statistic is time of no detectable disease (or to progression) as measured from the date of last treatment (i.e., period of no detectable disease). Measured thus, patients nos. 1 and 2 were disease-free for 23 months until progression. Patient #5 was disease-free for 24 months until progression. Patient #7 is still disease free after 22 months.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

TABLE 4

| Patient Characteristics | | | | | | | | |
|---|---|---|---|---|---|---|---|---|
| Patient No. | Age/Sex | Dosage (mg) | Origin Disease | Baseline CEA Level | Humoral Response | Cellular | On Study | Current Status |
| 1 | 66/M | 2 | colon | <3.0 ng/ml | + | + | 7/94 | progression after 22 mos. |
| 2 | 66/M | 2 | colon | <1.0 ng/ml | + | + | 9/94 | progression after 21 mos. |
| 3 | 20/F | 2 | colon | <3.0 ng/ml | + | + | 3/95 | progression after 24 mos. |
| 4 | 38/M | 2 | colorectal | <1.0 ng/ml | + | + | 5/94 | progression after 20 mos. |
| 5 | 68/F | 2 | lung | 4.5 ng/ml | + | + | 4/95 | progression after 23 mos. |
| 6 | 48/M | 2 | lung | <1.0 ng/ml | + | + | 3/94 | progression after 36 mos. |
| 7 | 55/M | 2 | colon | 22.0 ng/ml | + | + | 12/95 | no detectable disease |
| 8 | 47/F | 2 | appendix | <3.0 ng/ml | + | + | 5/96 | no detectable progression of initial minimal residual disease |
| 9 | 50/M | 2 | rectum | 8.8 ng/ml | + | + | 6/96 | no detectable disease |
| 10 | 40/F | 2 | colon | 3.9 ng/ml | + | + | 6/96 | progression after 6 mos. |
| 11 | 56/F | 2 | lung | <3.0 ng/ml | + | + | 6/96 | no detectable disease |
| 12 | 48/M | 2 | colon | 3.0 ng/ml | + | + | 7/96 | no detectable disease |
| 13 | 54/F | 2 | lung | 3.4 ng/ml | + | − | 7/96 | progression after 4 mos. |
| 14 | [ ]/F | 2 | lung | <3.0 ng/ml | N/A | N/A | 8/96 | progression within 1 mo. |
| 15 | 63/F | 2 | gastric | 0.5 ng/ml | + | to be determ. | 9/96 | no detectable disease |
| 16 | 64/F | 2 | lung | <3.0 ng/ml | to be determ. | to be determ. | 10/96 | no detectable disease |
| 17 | 30/F | 2 | colorectal | <3.0 ng/ml | + | to be determ. | 11/96 | no detectable disease |

Progression in the table indicates the time to progression as measured from the date of entering the study. The data show that of the 9 patients who have progressed, the range

What is claimed is:

1. A method of delaying development of a tumor which expresses CEA on the tumor cell surface in an individual with a low tumor burden, comprising administering an effective amount of anti-idiotype antibody 3H1 to the individual, wherein said administration results in the delay in development of the CEA-expressing tumor in the individual.

2. The method of claim 1, wherein the individual is high risk.

3. The method of claim 2, wherein the individual is in the adjuvant setting.

4. The method of claim 1, wherein 3H1 is administered with an adjuvant.

5. The method of claim 4, wherein the adjuvant is aluminum hydroxide.

6. The method of claim 1, wherein the tumor is of gastrointestinal origin.

7. The method of claim 6, wherein the tumor is colorectal.

8. The method of claim 1, wherein the tumor is lung.

9. The method of claim 1, wherein 3H1 is administered in an amount of about 1 mg to about 4 mg.

10. The method of claim 9, wherein 3H1 is administered in an amount of about 2 mg.

11. The method of claim 1, wherein 3H1 is administered at weekly intervals.

12. The method of claim 1, wherein 3H1 is administered every two weeks.

13. The method of claim 1, wherein 3H1 is heat-treated prior to administration.

14. The method of claim 1, wherein the individual has a circulating CEA level of less than about 50 ng/ml.

15. The method of claim 1, wherein 3H1 is administered at monthly intervals.

16. A method of treatment of a tumor which expresses CEA on the tumor cell surface in an individual with a low tumor burden comprising administering an effective amount of anti-idiotype antibody 3H 1 to the individual, wherein said administration results in treatment of said tumor.

17. The method of claim 16, wherein the individual is high risk.

18. The method of claim 17, wherein the individual is in the adjuvant setting.

19. The method of claim 16, wherein 3H1 is administered with an adjuvant.

20. The method of claim 19, wherein the adjuvant is aluminum hydroxide.

21. The method of claim 16, wherein the tumor is of gastrointestinal origin.

22. The method of claim 21, wherein the tumor is colorectal.

23. The method of claim 16, wherein the tumor is lung.

24. The method of claim 16, wherein 3H1 is administered in an amount of about 1 mg to about 4 mg.

25. The method of claim 24, wherein 3H1 is administered in an amount of about 2 mg.

26. The method of claim 16, wherein 3H1 is administered at weekly intervals.

27. The method of claim 16, wherein 3H1 is administered every two weeks.

28. The method of claim 16, wherein 3H1 is administered at monthly intervals.

29. The method of claim 16, wherein 3H1 is heat-treated prior to administration.

30. The method of claim 16, wherein the individual has a circulating CEA level of less than about 50 ng/ml.

31. A method of treatment of a tumor which expresses CEA on the tumor cell surface in an individual with a low tumor burden, said individual having a level of circulating CEA less than about 50 ng/ml, comprising administering an effective amount of anti-idiotype antibody 3H1 to the individual, wherein said administration results in treatment of said tumor.

32. The method of claim 31, wherein the individual is high risk.

33. The method of claim 32, wherein the individual is in the adjuvant setting.

34. The method of claim 31, wherein 3H1 is administered with an adjuvant.

35. The method of claim 34, wherein the adjuvant is aluminum hydroxide.

36. The method of claim 31, wherein the tumor is of gastrointestinal origin.

37. The method of claim 36, wherein the tumor is colorectal.

38. The method of claim 31, wherein the tumor is lung.

39. The method of claim 31, wherein 3H1 is administered in an amount of about 1 mg to about 4 mg.

40. The method of claim 39, wherein 3H1 is administered in an amount of about 2 mg.

41. The method of claim 31, wherein 3H1 is administered at weekly intervals.

42. The method of claim 31, wherein 3H1 is administered every two weeks.

43. The method of claim 31, wherein 3H1 is administered at monthly intervals.

44. The method of claim 31, wherein 3H1 is heat-treated prior to administration.

45. A method of treatment of a tumor which expresses CEA on the tumor cell surface of colon or colorectal origin in an individual with a low tumor burden comprising the steps of (a) administering 5-fluorouracil, (b) administering levamisole hydrochloride or leucovorin calcium; and (c) administering an effective amount of anti-idiotype antibody 3H1 to the individual, wherein said administration results in treatment of said tumor.

46. The method of claim 45, wherein the individual is high risk.

47. The method of claim 46, wherein the individual is in the adjuvant setting.

48. The method of claim 45, wherein 3H1 is administered with an adjuvant.

49. The method of claim 48, wherein the adjuvant is aluminum hydroxide.

50. The method of claim 45, wherein 3H1 is administered in an amount of about 1 mg to about 4 mg.

51. The method of claim 50, wherein 3H1 is administered in an amount of about 2 mg.

52. The method of claim 45, wherein 3H1 is administered at weekly intervals.

53. The method of claim 45, wherein 3H1 is administered every two weeks.

54. The method of claim 45, wherein 3H1 is administered at monthly intervals.

55. The method of claim 45, wherein 3H1 is heat-treated prior to administration.

56. The method of claim 45, wherein the individual has a circulating CEA level of less than about 50 ng/ml.

57. The methods of any one of claims 1, 16, 31, or 45, wherein said individual is human.

\* \* \* \* \*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

Ile Tyr Arg Ala Asn Arg Leu Ile Asp Gly Val
1               5                   10

(2) INFORMATION FOR SEQ ID NO: 2:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 2:

Pro Pro Ala Gln Tyr Ser Trp Leu Ile Asp Gly Asn
1               5                   10

(2) INFORMATION FOR SEQ ID NO: 3:

(i) SEQUENCE CHARACTERISTICS:
       (A) LENGTH: 447 base pairs
       (B) TYPE: nucleic acid
       (C) STRANDEDNESS: single
       (D) TOPOLOGY: linear (xi) SEQUENCE DESCRIPTION: SEQ ID NO: 3:

TCATATGGAT TACTAGTCGA CATGGTATCC ACAGCTCAGT TCCTTGGTAT CTTGTTGCTC      60

TGGTTTCCAG GTATCAAATC TGACATCAAG ATGACCCAGT CTCCATCTTC CATGTATGCA     120

TCTCTAGGAG AGAGAGTCAC GATCACTTGC AAGGCGAGTC AGGACATTAA TGGTTATTTA     180

AATTGGTTCC AACAAGAACC AGGGAAATCT CCTAAGACCC TGATCTATCG TGCAAATAGA     240

TTGATAGATG GGGTCCCATC AAGGTTCAGT GGCAGTGGAT CTGGGCAAGT TTACTCTCTC     300

ACCATCAGCA GCCTGGAATA TGAAGATATG GAACTTATT ATTGTCTACA GTTTGATGAG      360

TTTCCGTGGA TGTTCGGTGG AGGCACCAAG CTGGAAATCA AACGGGCTGA TGCTGCACCA     420

ACTGTCTCCA TCTTCCCACC ATCCAGT                                        447

(2) INFORMATION FOR SEQ ID NO: 4:

(i) SEQUENCE CHARACTERISTICS:
       (A) LENGTH: 142 amino acids
       (B) TYPE: amino acid
       (C) STRANDEDNESS: single
       (D) TOPOLOGY: linear (xi) SEQUENCE DESCRIPTION: SEQ ID NO: 4:

Met Val Ser Thr Ala Gln Phe Leu Gly Ile Leu Leu Leu Trp Phe Pro
1               5                   10                  15

```
Gly Ile Lys Ser Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
            35                  40                  45

Ile Asn Gly Tyr Leu Asn Trp Phe Gln Gln Glu Pro Gly Lys Ser Pro
        50                  55                  60

Lys Thr Leu Ile Tyr Arg Ala Asn Arg Leu Ile Asp Gly Val Pro Ser
65                  70                  75                  80

Arg Phe Ser Gly Ser Gly Ser Gly Gln Val Tyr Ser Leu Thr Ile Ser
                85                  90                  95

Ser Leu Glu Tyr Glu Asp Met Gly Thr Tyr Tyr Cys Leu Gln Phe Asp
            100                 105                 110

Glu Phe Pro Trp Met Phe Gly Gly Gly Thr Lys Leu Glu Ile Lys Arg
            115                 120                 125

Ala Asp Ala Ala Pro Thr Val Ser Ile Phe Pro Pro Ser Ser
        130                 135                 140
```

(2) INFORMATION FOR SEQ ID NO: 5:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (xi) SEQUENCE DESCRIPTION: SEQ ID NO: 5:

```
AGTCATATGG ATTGGGAATT CATGGAATGG AGCTGGGTCA TTCTCTTCCT CCTGTCAGGA    60

ACTGCAGGTG TCCACTCTGA GGTCCAGCTG CAACAGTCTG GACCTGAGCT GGTGAAGCCT   120

GGAGCTTCAC TGAAGATTTC CTGCGAGGCT TCTGGTTACT CACTCACTGC CTACACCATG   180

AACTGGGTGA AGCAGAGCCA TGGAAAGAGC CTTGAGTGGG TTGGGCTGAT TAATCCTTTC   240

AGTGGTGATA CTAACTACAG CCAGAAATTC ACGGGCAAGG CCACATTAAC TGTAGACAGG   300

TCATCCAGCA CAGCCTACAT GGAGCTCCTC AGTCTGACAT CTGAGGACTC TGCAGTCTAT   360

TACTGTGTCA TTACTCCGGT TCCCTACTGG TACTTCGATG TCTGGGGCGC AGGGACCACG   420

GTCACCGTCT CCTCAGCCAA AACGACACCC CCATCCGTCT AT                     462
```

(2) INFORMATION FOR SEQ ID NO: 6:

(i) SEQUENCE CHARACTERISTICS:
        (A) LENGTH: 147 amino acids
        (B) TYPE: amino acid
        (C) STRANDEDNESS: single
        (D) TOPOLOGY: linear (xi) SEQUENCE DESCRIPTION: SEQ ID NO: 6:

```
Met Glu Trp Ser Trp Val Ile Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Leu Lys Ile Ser Cys Glu Ala Ser Gly Tyr Ser Leu
        35                  40                  45

Thr Ala Tyr Thr Met Asn Trp Val Lys Gln Ser His Gly Lys Ser Leu
    50                  55                  60

Glu Trp Val Gly Leu Ile Asn Pro Phe Ser Gly Asp Thr Asn Tyr Ser
65                  70                  75                  80

Gln Lys Phe Thr Gly Lys Ala Thr Leu Thr Val Asp Arg Ser Ser Ser
```

```
                    85                  90                  95
Thr Ala Tyr Met Glu Leu Leu Ser Leu Thr Ser Glu Asp Ser Ala Val
            100                 105                 110
Tyr Tyr Cys Val Ile Thr Pro Val Pro Tyr Trp Tyr Phe Asp Val Trp
        115                 120                 125
Gly Ala Gly Thr Thr Val Thr Val Ser Ser Ala Lys Thr Thr Pro Pro
    130                 135                 140
Ser Val Tyr
145
```